United States Patent
Brown et al.

(10) Patent No.: US 10,478,154 B2
(45) Date of Patent: Nov. 19, 2019

(54) ULTRASOUND SENSOR ELEMENT, ULTRASOUND SENSOR ARRAY ASSEMBLY, ULTRASOUND TRANSMIT SENSOR ELEMENT, IMAGING DEVICE, ULTRASOUND TRANSDUCER, AND METHOD OF PERFORMING AN ULTRASOUND SCAN

(71) Applicant: Sharp Kabushiki Kaisha, Osaka (JP)

(72) Inventors: Christopher James Brown, Oxford (GB); Michael Robert Prior-Jones, Cambridge (GB); Benjamin James Hadwen, Oxford (GB)

(73) Assignee: Sharp Kabushiki Kaisha, Osaka (JP)

( * ) Notice: Subject to any disclaimer, the term of this patent is extended or adjusted under 35 U.S.C. 154(b) by 374 days.

(21) Appl. No.: 14/772,669

(22) PCT Filed: Mar. 7, 2014

(86) PCT No.: PCT/JP2014/001295
§ 371 (c)(1),
(2) Date: Sep. 3, 2015

(87) PCT Pub. No.: WO2014/136461
PCT Pub. Date: Sep. 12, 2014

(65) Prior Publication Data
US 2015/0374335 A1    Dec. 31, 2015

(30) Foreign Application Priority Data
Mar. 7, 2013    (GB) .................................. 1304149.6

(51) Int. Cl.
*A61B 8/14*    (2006.01)
*A61B 8/00*    (2006.01)
(Continued)

(52) U.S. Cl.
CPC .............. *A61B 8/4477* (2013.01); *A61B 8/14* (2013.01); *A61B 8/4455* (2013.01);
(Continued)

(58) Field of Classification Search
CPC ....... A61B 8/14; A61B 8/4281; A61B 8/4455; A61B 8/4488; A61B 8/4494; A61B 8/462; A61B 8/58; B06B 1/0207; B06B 2201/51
See application file for complete search history.

(56) References Cited

U.S. PATENT DOCUMENTS

| 4,694,434 A | 9/1987 | Von Ramm et al. |
| 5,901,708 A | 5/1999 | Chang et al. |

(Continued)

FOREIGN PATENT DOCUMENTS

| GB | 2453695 B | 2/2011 |
| JP | 01-164354 A | 6/1989 |

(Continued)

OTHER PUBLICATIONS

International Search Report for corresponding International Application No. PCT/JP2014/001295 dated Jun. 3, 2014.
(Continued)

*Primary Examiner* — Mark D Remaly
(74) *Attorney, Agent, or Firm* — Renner, Otto, Boisselle & Sklar, LLP

(57) ABSTRACT

Methods and apparatus for ultrasound imaging using ultrasound sensor elements comprising thin film transistors. Specifically, ultrasound elements for use in a two dimensional array of ultrasound elements, two dimensional arrays of ultrasound elements, ultrasound sensor element array assemblies, ultrasound imaging devices and methods of performing an ultrasound scan using a two dimensional array of ultrasound elements. A sensor element comprises:

(Continued)

an ultrasound transducer, a transmit circuit configured to provide an electrical signal to the transducer for output of an ultrasound signal; and a receive circuit configured to receive an electrical signal from the transducer, based on a received reflected ultrasound signal, wherein the transmit and receive circuits each comprise one or more thin film transistors.

12 Claims, 15 Drawing Sheets

(51) Int. Cl.
    *G01S 15/89*     (2006.01)
    *G01S 7/52*     (2006.01)
    *G10K 11/34*     (2006.01)

(52) U.S. Cl.
    CPC ........ *A61B 8/4494* (2013.01); *G01S 7/52079* (2013.01); *G01S 15/8925* (2013.01); *G01S 15/8993* (2013.01); *G10K 11/341* (2013.01)

(56) References Cited

U.S. PATENT DOCUMENTS

| | | | | |
|---|---|---|---|---|
| 2007/0016022 A1* | 1/2007 | Blalock | ............... | G01S 7/52028 600/437 |
| 2007/0066897 A1* | 3/2007 | Sekins | ................... | A61B 5/445 600/437 |
| 2012/0130246 A1* | 5/2012 | Haider | ................. | A61B 8/4477 600/447 |
| 2012/0144920 A1 | 6/2012 | Wong et al. | | |
| 2012/0197132 A1* | 8/2012 | O'Connor | ............ | A61B 8/0891 600/461 |

FOREIGN PATENT DOCUMENTS

| | | |
|---|---|---|
| JP | 03-247324 A | 11/1991 |
| JP | 2004-057532 A | 2/2004 |
| JP | 2005-040376 A | 2/2005 |
| JP | 2009-261611 A | 11/2009 |
| WO | WO 2007/095390 A2 | 8/2007 |

OTHER PUBLICATIONS

Form PCT/ISA/237 for corresponding International Application No. PCT/JP2014/001295 dated Jun. 3, 2014.

Y.Kato et al., A Large-Area, flexible, ultrasonic imaging system with a printed organic transistor active matrix, p. 1-4.

Y.Kato et al., A Large-Area Flexible Ultrasonic Imaging System With an Organic Transistor Active Matrix, IEEE Transactions on Electron Devices, vol. 57, No. 5, p. 995-1002.

* cited by examiner

Etch Sacrificial Polymer

ULTRASOUND SENSOR ELEMENT, ULTRASOUND SENSOR ARRAY ASSEMBLY, ULTRASOUND TRANSMIT SENSOR ELEMENT, IMAGING DEVICE, ULTRASOUND TRANSDUCER, AND METHOD OF PERFORMING AN ULTRASOUND SCAN

TECHNICAL FIELD

The invention relates to methods and apparatus for ultrasound imaging using two dimensional arrays of ultrasound sensor elements. Further, the invention relates to, but is not limited to, ultrasound elements for use in a two dimensional array of ultrasound elements, two dimensional arrays of ultrasound elements, Ultrasound sensor element array assemblies, ultrasound imaging devices and methods of performing an ultrasound scan using a two dimensional array of ultrasound elements.

BACKGROUND ART

Driving forces in the development of ultrasound imaging technology include the need for point-of-care imaging (e.g. by general practitioners or other deliverers of primary healthcare) and the introduction of clinical applications requiring three dimensional (3D) and four dimensional (4D) ultrasound imaging. As a result, there are trends towards the use of ultrasound probes with two dimensional (2D) arrays of ultrasound sensor elements and the miniaturization of probes through closer integration of the transducer and control electronics.

U.S. Pat. No. 4,694,434 describes an ultrasound imaging device with a 2D array of transmit and receive elements that is capable of generating 3D images. More recently, "Integration of 2D CMUT Arrays with Front-End Electronics for Volumetric Ultrasound Imaging", Wygant et al (2008) describes an ultrasound imaging device with a 2D transducer array integrated on a silicon integrated circuit.

US Patent Application 2012/0144920 describes an ultrasound imaging device utilizing thin-film transistors to form an array of receive circuits.

WO2007/095390 proposes a TFT device with an integrated piezo-electric layer to generate or receive ultrasound signals, and also proposes an array comprising elements each containing one of these devices and a TFT switch.

GB2453695 proposes an ultrasound array with TFT devices, and suggests a TFT as a switch or amplifier in each element of the array.

CITATION LIST

Patent Literature

PTL 1: U.S. Pat. No. 4,694,434
PTL 2: US Patent Application 2012/0144920
PTL 3: WO2007/095390
PTL 4: GB2453695

SUMMARY OF INVENTION

According to the present invention, there is provided an ultrasound sensor element for use in a two dimensional array of ultrasound sensor elements, the sensor element comprising: an ultrasound transducer, a transmit circuit configured to provide an electrical signal to the transducer for output of an ultrasound signal; and a receive circuit configured to receive an electrical signal from the transducer, based on a received reflected ultrasound signal, wherein the transmit and receive circuits each comprise one or more thin film transistors.

According to the present invention, there is provided an ultrasound transmit sensor element for inclusion in a two dimensional array of ultrasound sensor elements, the sensor element comprising: an ultrasound transducer, a transmit circuit comprising one or more thin film transistors and configured to provide an electrical signal to the transducer for output of an ultrasound signal; and a delay circuit configured to delay a transmit signal for the ultrasound transducer.

According to the present invention, there is provided an ultrasound transducer comprising: a micro-electro-mechanical system portion vibratable for emitting an ultrasound signal; and a thin film transistor portion configured to drive electro-statically the micro-electro-mechanical system portion to cause it to vibrate.

According to the present invention, there is provided a method of performing an ultrasound scan using a two dimensional array of sensor elements, the method comprising: defining a sub-aperture of sensor elements in a first location within the array of sensor elements; transmitting an ultrasound signal and receiving reflected ultrasound signals using the sensor elements of the sub-aperture at the first location; shifting the sub-aperture to a second location within the array of sensor elements; and transmitting an ultrasound signal and receiving reflected ultrasound signals using the sensor elements of the sub-aperture at the second location.

According to the present invention, there is provided an ultrasound imaging device comprising: a two dimensional array of ultrasound sensor elements configured to emit ultrasound signals and receive reflected ultrasound signals; and a display positioned on a non-emitting side of the array.

According to the present invention, there is provided an ultrasound imaging device comprising: a two dimensional array of ultrasound sensor elements configured to emit ultrasound signals and receive reflected ultrasound signals, wherein the array is conformable, such that it may conform at least partially to the contours of a surface against which it is placed.

BRIEF DESCRIPTION OF DRAWINGS

Exemplary embodiments of the invention are disclosed herein with reference to the accompanying drawings, in which.

DESCRIPTION OF EMBODIMENTS

To mitigate or overcome some of the problems in the prior art, disclosed herein are ultrasound imaging devices based on a flat-panel probe in which the transmit and receive circuits are formed in a large 2D array using thin-film transistors. Such a device brings two key benefits from a clinical point-of-view.

Firstly, a display may be mounted onto the back of the flat panel probe. This allows the clinician to "look" directly into the patient making it easy to identify what is being imaged and to take appropriate measurements. Such a device is expected to be of use in the primary care and point-of-care markets where users are semi-skilled with some knowledge of anatomy but limited training in the use of ultrasound imaging equipment.

Secondly, the flat panel probe may be manufactured on a flexible substrate or many flat panel probes may be assembled into an array to create a large conformable imaging device. Such a device may simply be laid on top of a patient by an unskilled operator without regard to exact orientation or position. The device may automatically control the image generation process without the need for intervention by the operator. Automation of the image generation and analysis processes may be achieved either by expert software or by a remote operator.

Generally, the methods and apparatus disclosed herein comprise system architectures and circuit designs to create a thin film transistor (TFT) based ultrasound imaging device. Due to the relatively poor performance and large size of TFTs compared to standard silicon metal-oxide-silicon (MOS) transistors, it is challenging to integrate all of the functionality of the ultrasound transmit and receive circuits into a single ultrasound sensor element. In particular, the size of the circuits required to implement an analogue delay used to focus (or steer) an ultrasound signal emitted from an array of ultrasound elements is too large to integrate easily into a sensor element circuit using TFTs. The system architecture disclosed herein allows the signal generating circuits to be divided between a sensor element circuit and an active matrix array with no significant loss in performance. This is a key enabling technology for TFT based ultrasound systems.

Figure 1A:
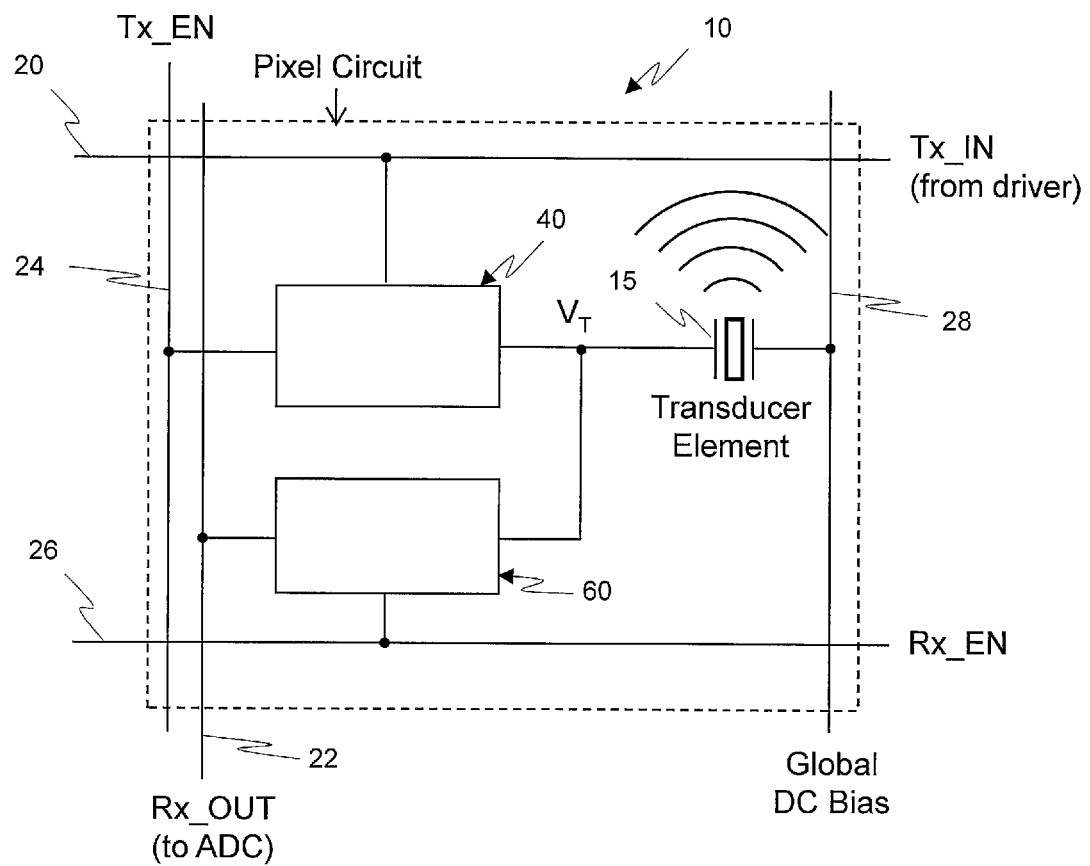
FIG. 1a is a schematic diagram of an ultrasound sensor element.

In accordance with a most general embodiment of the present invention FIG. 1a shows a schematic diagram of an ultrasound sensor element 10 comprising an ultrasound transducer element 15, a transmit circuit 40 and a receive circuit 60. The transmit circuit 40 may be in electrical communication with a transmit input signal line 20 and a transmit enable signal line 24. The transmit circuit 40 may therefore be controlled to selectively connect the transmit input signal to the ultrasound transducer element 15 in order to generate an ultrasonic output. The receive circuit 60 may be in electrical communication with a receive output signal line 22 and a receive enable signal line 26. The receive circuit may therefore be controlled to selectively measure the ultrasonic input signal received by the transducer element on the receive output signal line. The transmit input signal line and transmit enable signal line may be arranged in perpendicular direction to each other so that any sensing element in the array may be uniquely activated. The receive output signal line and receive enable signal line may be arranged in perpendicular direction to each other so that any sensing element in the array may be uniquely measured.

In an exemplary mode of operation, the transmit and receive circuits are enabled time-sequentially. In a first transmit period the receive circuit 60 is disabled, the transmit circuit 40 is enabled and a transmit input signal is applied to the transmit input signal line 20 such that an ultrasonic signal is generated by the transducer element 15. In a subsequent second receive period the transmit circuit 40 is disabled, the receive circuit 60 is enabled and the transducer element 15 converts the ultrasonic signal incident on it to an electrical signal which is measured on the receive output signal line 26.

Figure 1B:
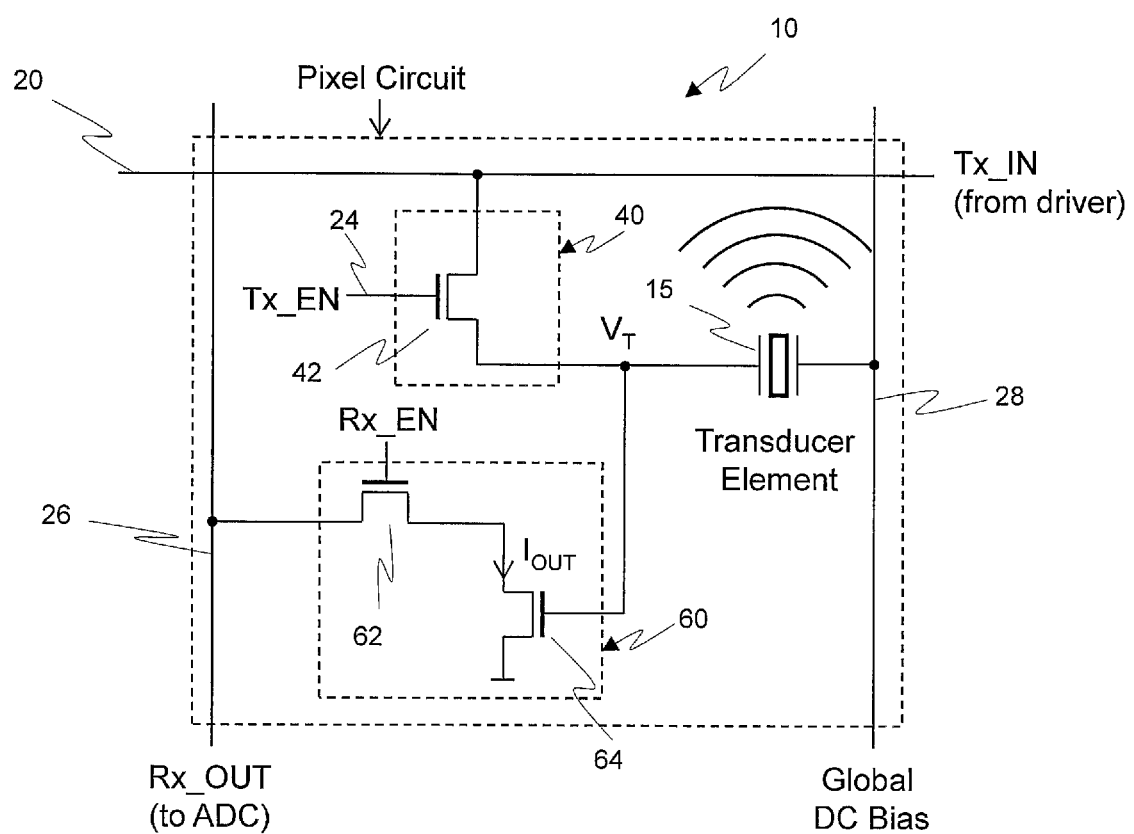
FIG. 1b is circuit diagram showing an exemplary ultrasound sensor element.

FIG. 1b shows a schematic diagram illustrating a most basic TFT implementation of the ultrasound sensor element 10. The transmit circuit 40 comprises a single transmit switch TFT 42 which may be arranged with its gate terminal connected to the transmit enable signal line 24, its drain terminal connected to the transmit input signal line 20 and its source terminal connected to the transducer element 15. The receive circuit may also comprise a single switch TFT with its gate terminal connected to the receive enable signal line, drain connected to the received output signal line and source connected to the transducer element. Alternatively, as shown in FIG. 1b, the receive circuit may include both a receive switch TFT 62 and a receive amplifier TFT 64. The gate terminal of the amplifier TFT 64 may be connected to the transducer element 15 thus providing a transconductance gain between the voltage signal, $V_T$, generated by the transducer element due to the received ultrasonic signal, and the output current, $I_{OUT}$, that is measured on the receive output signal line 22 when the receive switch TFT 62 is enabled.

The use of TFTs allows arrays to be manufactured that have large array sizes. This, in turn, allows full electronic image generation without the need to move the array or, more accurately, an ultrasound probe comprising the array. It is possible to make a large array size using conventional silicon based micro-electronics (e.g. wafer size up to 12" diameter are standard in the industry) but the processing is more complicated and the cost is significantly higher than using a TFT process. TFT processes are suitable for use with large area substrates (e.g. up to 3 m×3 m in size) and the cost per unit area is much lower than silicon based processes.

Further, conventional silicon based processes are limited to operate at a maximum of approximately 5 volts. Operating at higher voltages may result in damage to the transistors in silicon based integrated circuits (ICs). There are niche silicon IC processes that can operate at higher voltages, up to the requirements of ultrasound transducers, but these are expensive and the resulting transistors have a worse performance than standard silicon ICs. TFTs are able to operate at significantly higher voltages and are therefore suitable for driving ultrasound transducers.

Further still, TFTs may be fabricated using low temperature processes compatible with glass or plastic substrates. As a result, cost is reduced and there is the possibility to make a flexible imaging device that can conform to the contours of, for example, a human subject.

Figure 2A:
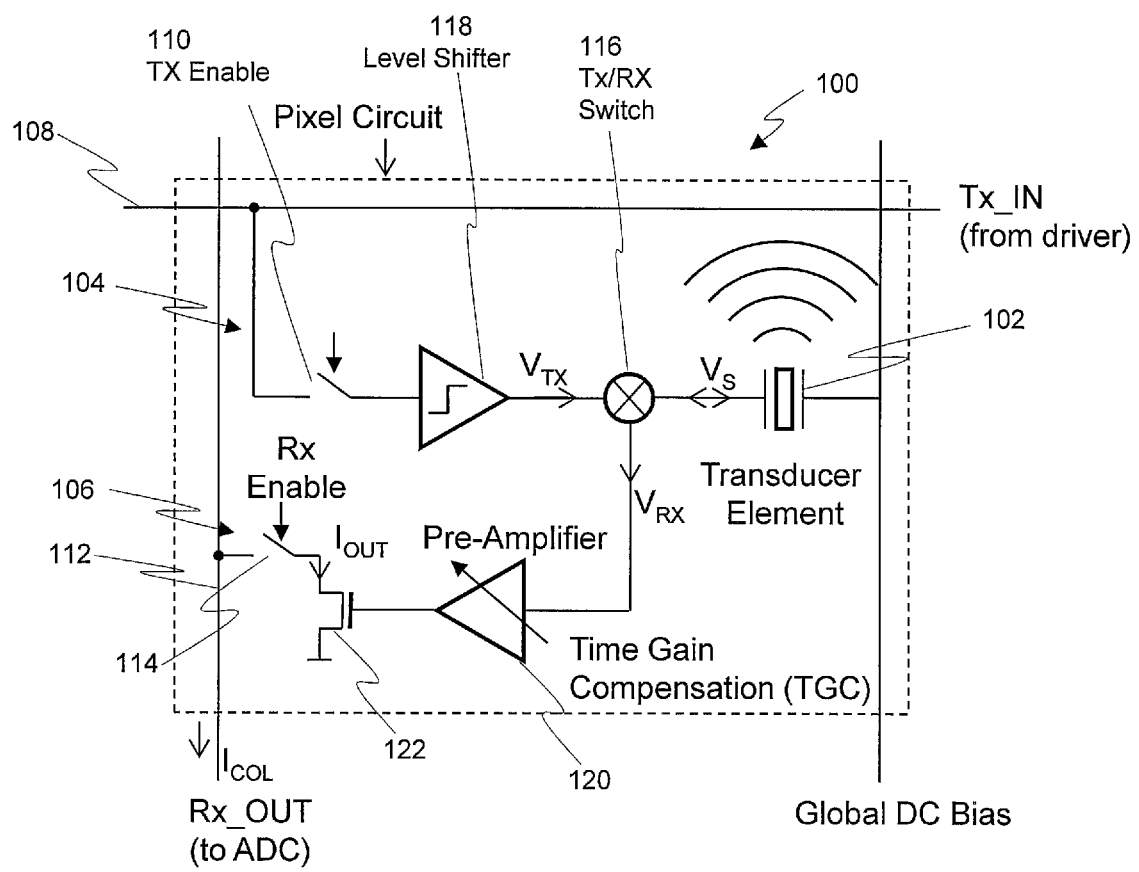
FIG. 2a is a schematic diagram of an ultrasound sensor element.

FIG. 2a shows a schematic diagram of an alternative ultrasound sensor element 100 comprising an ultrasound transducer 102, a transmit circuit 104 and a receive circuit 106. The ultrasound sensor element 100 includes additional circuit elements to enhance the signal-to-noise ratio of the imaging device and hence improve the output image quality. The transmit circuit 104 may be in electrical communication with a transmit line 108 via a transmit enable switch 110. Therefore, the transmit circuit 104 is selectively connected to the transmit line 108, and may be selectively enabled, by operation of the switch 110. Similarly, the receive circuit 106 may be in electrical communication with a receive line 112 via a receive enable circuit. In this embodiment the receive enable circuit is constituted by a receive enable switch 114, but other receive enable circuits may be used. Therefore, the receive circuit is selectively connected to the receive line, and may be selectively enabled, 112 by operation of the receive enable circuit (that is, by operation of the receive enable switch 114). Selective enablement of the transmit and receive circuits 104, 106 allow the use of sub-apertures when performing ultrasound scans, as explained below.

The transmit circuit 104 and the receive circuit 106 are each selectively connected to the ultrasound transducer 102 by a transmit/receive switch 116. The transmit/receive switch may be configured to toggle between connection of the transducer 102 to the transmit circuit 104 or the receive circuit 106.

The transmit circuit 104 comprises a level shifter 118. An input of the level shifter 118 is in electrical communication with the transmit selection switch 110. An output of the level shifter 118 is in electrical communication with the transmit/receive switch 116. The level shifter 118 is configured to receive a first voltage being a digital level voltage (e.g. in a range from 2 to 5 volts) and convert that voltage to a second voltage being a voltage sufficient to drive the transducer 102 (typically 10 to 50 volts). The transmit circuit 104 comprises one or more TFTs and specific transmit circuits are manufactured exclusively from TFTs.

The receive circuit 106 comprises a pre-amplifier 120. An input to the pre-amplifier 120 is in electrical communication with the transmit/receive switch 116. An output of the pre-amplifier 120 is in electrical communication with a gate of an output transistor 122. A receive enable circuit is provided for selectively enabling the receive circuit, and in the embodiment of FIG. 2a this is constituted by receive enable switch 114. When the receive circuit is enabled by closing the receive enable switch 114 the drain of the output transistor 122 is in electrical communication with the receive output signal line 112. The pre-amplifier 120 may be configured to apply time-gain compensation to a received signal. That is, the pre-amplifier 120 may be configured to adjust its gain over time so that weaker reflected signals that are received later are amplified more than stronger reflected signals that are received earlier. The output transistor 122 is configured to be "on" (i.e. to conduct) when the pre-amplifier 120 outputs a sufficiently high voltage (i.e. when a signal is received by the receive circuit 106). The receive circuit 106 comprises one or more TFTs and specific receive circuits are manufactured exclusively from TFTs.

The ultrasound transducer 102 is in electrical communication with the transmit/receive switch 116. The ultrasound transducer 102 is configured to receive an electrical signal from the transmit circuit 104 and emit an ultrasound signal. The ultrasound transducer is configured to receive a reflected ultrasound signal and emit an electrical signal into the receive circuit 106. As explained in greater detail below, the transducer 102 may be a micro-electro-mechanical system (MEMs) transducer and, in a specific transducer 102, may be a capacitive micromachined ultrasonic transducer (CMUT).

Exemplary sensor elements 100 may be 250 micro meter square. Exemplary sensor elements may operate at a frequency in a range from 1 MHz to 10 MHz.

Figure 2B:
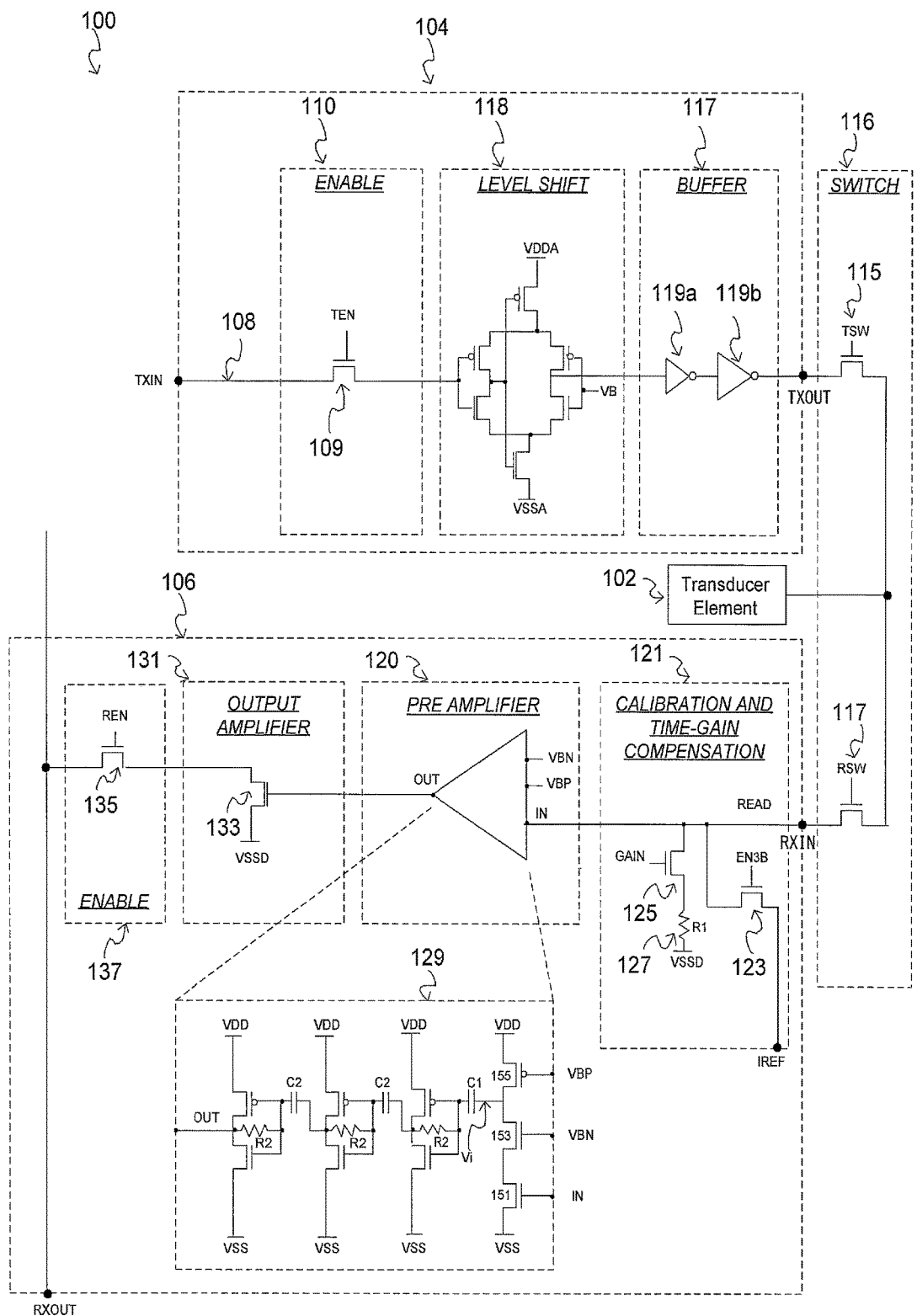
FIG. 2b is circuit diagram showing an exemplary ultrasound sensor element.

As set out above, the transmit circuit 104 and receive circuit 106 are integrated into the sensor elements 100 that may form an active matrix array. An example sensor element for an active matrix array in an ultrasound imaging system is shown in FIG. 2b. A transmit-receive (Tx/Rx) switch 116 may also be used to connect the transducer 102 to either the transmit circuit 104 or the receive circuit 106. It is possible to construct the system such that the delay function on transmit and/or receive is implemented by driver circuits at the edge of the active matrix (discussed below). It is therefore not necessary to include any delay elements in the pixel circuit itself.

The transmit circuit 104 may be configured to receive an input signal, TXIN, and produce an output signal, TXOUT. Referring to FIG. 2a and FIG. 2b, the transmit circuit may contain: an enable circuit 110; a level shift circuit 118; a buffer amplifier 117; and output enable (or transmit/receive) switch 116. The overall function of the transmit circuit 104 is to selectively supply a suitable drive signal TXOUT, which is based on the input signal TXIN, to the transducer element 102. The input signal TXIN may supplied via transmit line 108, which may be common to all elements within the same row.

The input signal TXIN will typically consist of a time varying voltage signal. The input signal TXIN may typically be a voltage waveform of frequency in the range 1-10 MHz. The input signal TXIN may typically be a sinusoidal signal or alternatively may be a square wave voltage signal. The input signal TXIN may typically have an amplitude in the range 1-5V, compatible for example with a signal that may be generated by a standard IC fabricated in a standard CMOS process.

The enable circuit 110 may for example consist of a switch transistor 109, which enables the input TXOUT to be connected to the input of the level shift circuit 118 when a transmit enable control signal TEN is taken high. Therefore, the transmit circuit 104 is selectively enabled, by operation of the switch 110.

The level shift circuit 118 may be configured to amplify the voltage signal at its input to produce a voltage signal at its output of increased amplitude. The voltage amplitude of the level shift circuit 118 output may, for example, be chosen to correspond to the voltage amplitude that is necessary to drive the transducer element 102 so as to emit ultrasound pulses from the transducer element 102. This voltage amplitude may for example be in the range 10-50V. The level shift circuit 118 may for example be a digital circuit whose output is either at a voltage high (i.e. a "1") or a voltage low level (i.e. a "0"). The level shift circuit 118 may for example consist of a comparator circuit, as shown for example in FIG. 2b. The comparator circuit of this example works by comparing the voltage signal at its input to a reference input signal VB and producing an output signal at a high voltage level at times when the input voltage exceeds VB and an output signal at a low voltage level when the voltage signal at its input is less than the reference input signal VB.

The output of the level shifter circuit 118 is connected to a buffer amplifier 117. The function of the buffer amplifier is to buffer the digital output of the level shift circuit 118 such that it is capable of driving an electronic load presented by the transducer element 102. The buffer amplifier 117 may, for example, be composed of two inverter circuits 119a and 119b the component devices of which may be chosen such that output current supplied is sufficient to drive the capacitive load presented by the transducer element 102.

The transmit/receive switch 116 may consist, for example, of two switch transistors 115 and 139 which may be controlled by transmit switch control signal TSW and receive switch control signal RSW. Transmit switch control signal TSW may for example be common to all array elements within the same row of the array, or alternatively may be common to all array elements within the same column of the array. Likewise, transmit switch control signal TSW may for example be common to all array elements within the same row of the array, or alternatively may be common to all array elements within the same column of the array.

The transmit/receive switch 116 may be configured to toggle between connection of the transducer 102 to the transmit circuit 104 or the receive circuit 106, such that the transducer element 102 may be connected to either the output signal TXOUT of the transmit circuit 104 or to the input signal RXIN of the receive circuit 106.

The receive circuit 106 may contain: a calibration and time-gain compensation circuit 121; a signal pre-amplifier 120; an output amplifier 131; and an output enable switch 137. The basic function of the receive circuit is to detect and amplify an input signal RXIN received from the transducer element 102. The operation of an exemplary implementation of the receive circuit 106 is now described.

The preamplifier 120 performs the function of amplifying and buffering the signal RXIN at its input IN. An example implementation of the pre-amplifier circuit is shown as pre-amplifier example circuit 129 in FIG. 2b. According to this example the pre-amplifier circuit comprises an input stage and amplification stages. The input stage comprises an input transistor 151 and bias transistors 153 and 155. The current through the bias transistors 153 and 155 is controlled by input voltage signals VBN and VBP which may be common to all elements within the array. The input stage is responsible for modifying the DC level of the time varying input signal IN to create a voltage signal at the node marked Vi whose DC offset level is approximately halfway between the power supply biases VDD and VSS. The amplification stage of the exemplary circuit 129 consists of a chain of inverter stages, in the example shown this comprises three inverter stages. Each inverter stage is AC coupled from the next stage by capacitors C1 and C2. Each inverter also has a resistor R2 connected between its input and its output so that each stage functions in effect as a transimpedance amplifier. The overall function of cascading multiple transimpedance stages is to amplify the voltage signal swing such that the output signal OUT has a larger voltage signal swing than the input IN. The overall function of the preamplifier exemplary circuit 129 is to amplify the voltage signal. The value of the coupling capacitor C1 may typically be of order 20 fF and the value of coupling capacitors C2 may typically be of order 100 fF. The value of resistor R2 will typically be of order 1 MOhm.

The architecture of the pre-amplifier circuit 129 should be regarded as exemplary, but will be appreciated as an example circuit that is well suited to implementation with TFTs. Additionally such a design of pre-amplifier circuit as 129 can be realised with a relatively small number of circuit components and is furthermore capable of providing a high factor of amplification with good linearity of response.

The output OUT of the pre-amplifier circuit 120 is connected to an output amplifier 131. The output amplifier 131 may be configured so as to convert the voltage output OUT into a current output IOUT. A simple implementation of the output amplifier 131 may be by use of a single transistor 133. The voltage output from the pre-amplifier 120 is connected to the gate of transistor 133, whilst the source of transistor 133 is connected to a DC supply voltage VSSD. Accordingly an output current can be made to pass through transistor 133 when the output RXOUT is appropriately biased, for example by means of a bias voltage signal supplied from a source external to the sensor array. By measurement of the output current supplied through RXOUT, a measurement is made in effect of the voltage at the receive circuit input RXIN.

Additionally an optional enable circuit 137 may be included. Such a circuit may consist of a switch transistor 137, which may be controlled by a receive enable control signal REN which may for example be common to all elements within the same row of the array. The purpose of the enable circuit is to allow the output of one or more receive circuits 106 to be summed onto the output RXOUT which may be common to all elements within the same column of the array.

The receive circuit 106 may also optionally contain a calibration and time-gain compensation circuit 121. An exemplary implementation of time-gain compensation circuit is also shown in FIG. 2b. According to this implementation a reference input signal IREF may optionally be connected to the input IN of the pre-amplifier circuit by means of switch transistor 123. The reference input signal IREF may be used to perform a calibration of the receive circuit 106, i.e. by applying an input signal IREF of known amplitude and measuring the output signal RXOUT the gain of each individual receive circuit may be calculated. This calculated gain may be stored and subsequently used to calibrate the output signal.

The calibration and time-gain compensation circuit 121 may optionally also contain a range select function for varying the gain of the pre-amplifier. An example circuit implementation of such a function is also shown in the diagram of FIG. 2b and comprises a select switch transistor 125 and a resistor 127 of value R1. The value of R1 may typically be in the range 1 k ohm to 10 k ohm. When the input GAIN, which is supplied to the gate of transistor 125 is taken high, the resistor R1 is connected between IN and a DC supply VSSD. The overall effect is to increase the impedance presented at the input IN of the pre-amplifier 120. This has the effect of suppressing the gain of the pre-amplifier.

Figure 2C:
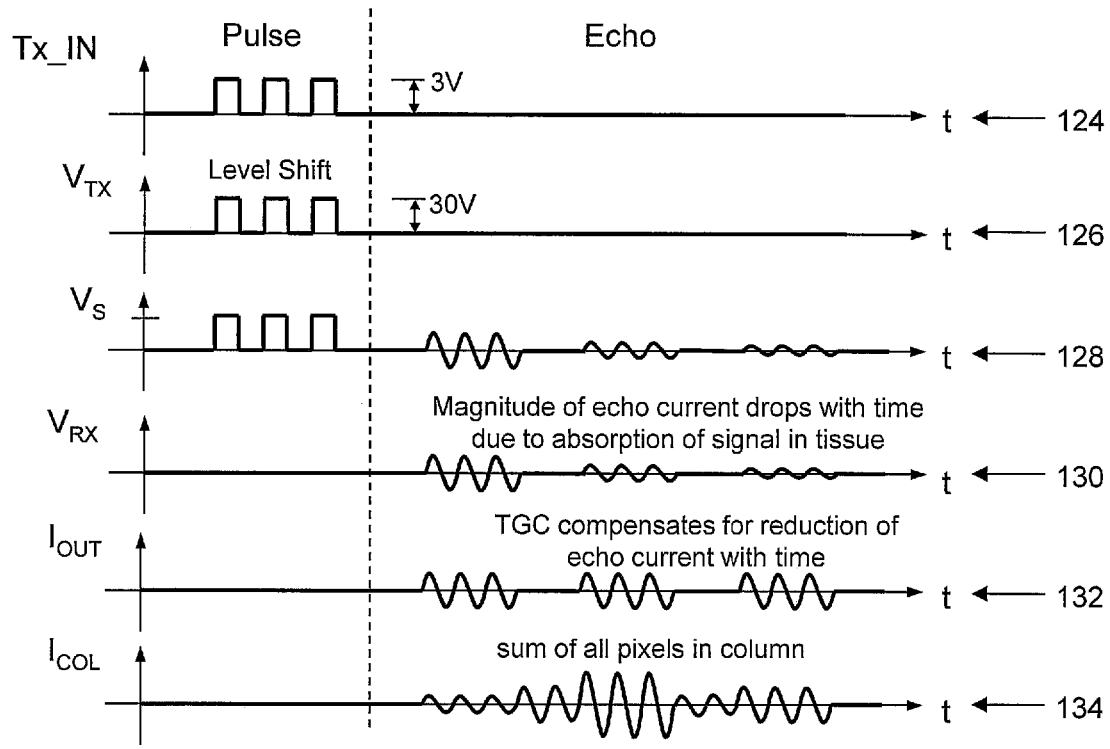
FIG. 2c is a signal timing diagram.

Further description of the operation of the ultrasound element 100 as shown in FIG. 2b may be provided with reference to the timing diagram shown in FIG. 2c. The circuit operates in two phases, a transmit phase during which the transmit circuit 104 is activated, and a receive phase during which the receive circuit 106 is activated.

During the transmit phase, the control signals TEN and TSW may be taken high on array elements containing a transducer to be actuated. As a result, transistors 109 and 115 of the relevant array elements are turned on. Transistor 139 is also turned off (by means of control signal RSW) to isolate initially the receive circuit 106 from the transducer element 102 within the ultrasound element 100 being considered. A voltage pulse, for example a square wave pulse of 3V amplitude may be externally generated and applied to TXIN, as shown by trace 124 in FIG. 2c. The transmit circuit 104 functions so as to amplify this voltage pulse and apply a high voltage pulse (e.g. of amplitude 30-50V as shown in trace 126) to the transducer element 102. The transducer element 102 may thus function to generate ultrasound pulses of frequency and amplitude determined by the frequency and voltage of the driving signal. The operation and possible implementations of example transducer elements are described later.

The switch transistors 109 and 115 may be independently driven (by control signals TEN and TSW). Therefore it is possible to vary the timings of voltage pulses applied to different ultrasound elements 100 in the array, for example within one row of the array elements in different columns may have voltages supplied to the individual transduce elements 102 at different times. Therefore it is possible to create timing delays without the requirement to have any specific delay generating circuitry within transmit circuit 104 within the array element 100. The importance of this for controlling the generated ultrasound beams will be further explained shortly.

At the end of the transmit phase, switch transistors 109 and 115 may both be turned off so that the transducer element 102 is electrically isolated from the transmit circuit 104. At the same time, transistor 139 may be turned on by means of control signal RSW to enable the receive circuit 106 of the ultrasound element 100. During the subsequent time of operation the ultrasound element 100 is thus configured to detect ultrasound signals that are now being received by the transducer elements 102. Such ultrasound signals are converted into electrical signal (a current by the transducer element 102). This electrical current may then be detected by the detection circuitry 106.

The emitted ultrasound beam is reflected from items in the path of the beam and received by the transducer 102. The ultrasound beam may be emitted, for example, into a human or animal subject. By measurement of the time and space variation of the reflected signal it is possible to reconstruct the path taken by the ultrasound and therefore to create a 3D image of the internal features of the body.

In a typical application the transducer element 102 of a given ultrasound element 100 in the array may be first configured so as to emit ultrasound pulses and then switched into a mode so as to be able to detect received ultrasound signals, as shown by trace 128 in FIG. 2c.

In receive mode, the transducer 102 may detect signals reflected back by some external body (for example human tissue). The receive circuit 106 may be further configured such that the gain of the sensor circuit is changed at some time part way through the measurement of the received signal. For example in a typical application, the received echo signal becomes weaker over time. This is because the received signal after a short time is echoed from objects nearby and is stronger than the received signal after a long time which has been echoed from objects that are further away. In a typical application the receive circuit 106 may begin detecting in a low gain mode (for example with signal GAIN in FIG. 2b set high) and at a later time switched to a high gain mode (signal GAIN set low). Such a mode of implementation may be advantageous to avoid saturating the detection circuits with the initial large amplitude signal whilst also being sensitive to the low amplitude signals that are received at a later time.

Compared to a more conventional approach in which wires are used to connect each transducer element in a probe head to circuits in a probe body or separate signal processing box, the use of an active matrix array has several advantages.

Firstly, with transmit amplifiers (level-shifters) in each pixel a low voltage (e.g. 3V) signal can be applied to the transmit lines 108. This may then be amplified within the pixel circuit to e.g. 50V to drive the transducer element 102. Since it is not necessary to drive large capacitive loads at high voltages, a significant reduction in the power consumption of the system can be achieved (dynamic power consumption, $P=CV^2f$).

Secondly, the in-element receive amplifier 120 significantly increases the signal-to-noise (SNR) ratio of the system. A high SNR is important for high image quality since it allows features with a low signal profile to be imaged in more detail. These features may be smaller in size, have a smaller difference in acoustic impedance than the surrounding tissue or be deeper in the body.

The ultrasound beam may be emitted, for example, into a human or animal subject to form an image of internal features of the body.

The emitted ultrasound beam is reflected from items in the path of the beam and received by the transducer 102. The transducer 102 converts a received ultrasound signal into an electrical signal. The electrical signal representing the received ultrasound signal passes through 130 the transmit/receive switch 116, which has been toggled to be set to receive, and is received at an input to the pre-amplifier 120. The pre-amplifier 120 amplifies the electrical signal (possibly according to time-gain compensation) and outputs 132 an current ($I_{OUT}$). The amplified electrical signal is received at the gate of the output transistor 122, which is thereby switched on. The output current is summed 134 with other output currents ($I_{COL}$) at the receive line 112 and passed to an analogue to digital converter (ADC).

Figure 3:
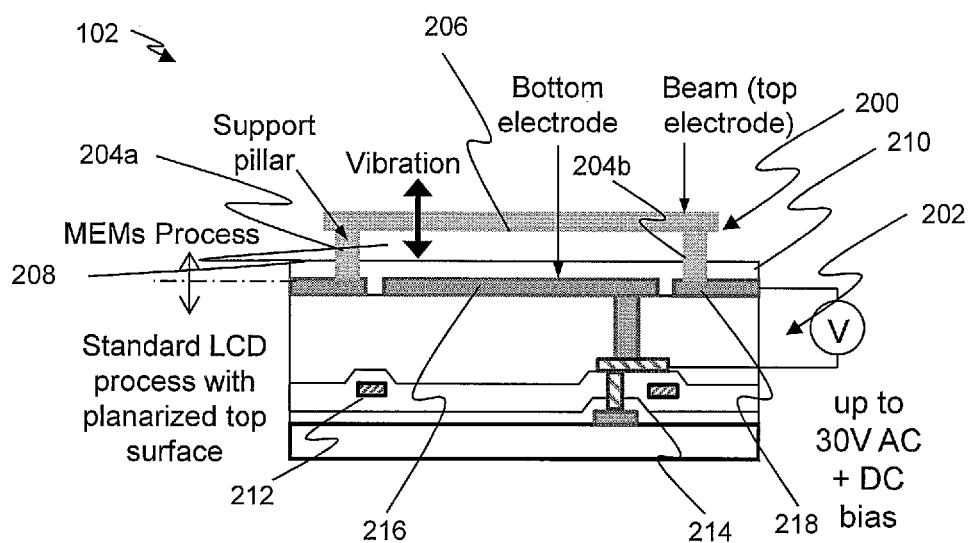
FIG. 3 is a schematic diagram of an ultrasound transducer.

FIG. 3 shows an ultrasound transducer 102 comprising a MEMs portion 200 vibratable for emitting an ultrasound signal and a TFT portion 202 configured to drive electrostatically the MEMs portion 200.

The MEMs portion 200 comprises a plurality of supporting pillars 204a, 204b, which support a beam member 206. The beam member 206 is able to vibrate across its span. The MEMs portion 200 is positioned on the TFT portion 202.

The supporting pillars 204a, 204b, the beam member 206 and an upper surface of the TFT portion 202 define a cavity 208. The cavity 208 may comprise a vacuum. The upper surface of the TFT portion 202 may be formed by an insulation layer 210 deposited on the top of the TFT portion 202.

The TFT portion comprises a gate electrode 212 and a source electrode 214. The source electrode 214 is connected to a first section of a conductive layer 216 forming a bottom electrode of the transducer 102. The beam member 206 forms an upper electrode of the transducer 102. The supporting pillars 204a, 204b are connected to a second section of a conductive layer 218, which is electrically isolated from the bottom electrode 216 by the insulation layer 210.

When a voltage is applied across the first and second sections of the conductive layer 216, 218, the electrical potential between the bottom electrode (conductive layer) 216 and the top electrode (beam) 206 is changed, which causes the top electrode to vibrate and causes the emission of an ultrasound signal. Conversely, if an ultrasound signal is incident on the top electrode 206, the top electrode 206 will vibrate causing a variation in the capacitance between the top electrode 206 and the bottom electrode 218, which generates a current or voltage signal in the TFT portion 202.

Figure 4A:
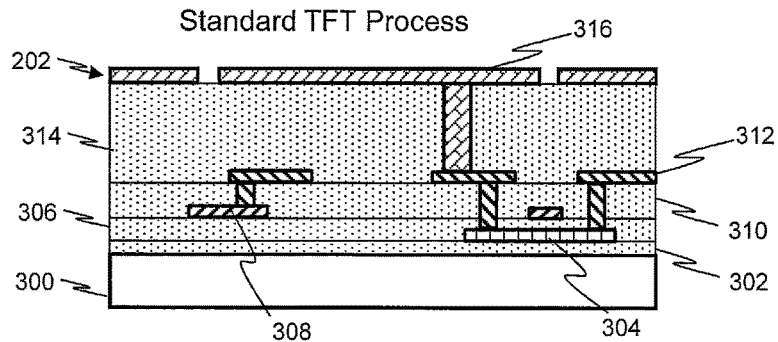
FIG. 4a shows the steps in fabricating an ultrasound transducer.

FIG. 4a-FIG. 4f show steps of manufacture of a MEMs/TFT ultrasound transducer 102. FIG. 4a shows the result of a standard TFT process to produce a TFT portion 202. These steps are described briefly below.

A base-coat insulator layer 302 (e.g. silicon nitride and/or silicon dioxide) is deposited onto a glass substrate 300.

Amorphous silicon is deposited onto the base-coat and re-crystallized to form poly-silicon 304 by laser re-crystallization or annealing. The poly-silicon layer 304 is then patterned using photolithography and etched to form islands corresponding to the individual transistors.

An insulator (silicon dioxide), known as the gate insulator 306, is deposited on top of the poly-silicon.

A first metal layer, known as the gate electrode layer 308, is then deposited on the gate insulator 306 and patterned.

Another insulator (silicon nitride and/or silicon dioxide), known as the interlayer dielectric layer 310, is then deposited on top of the gate insulator 306. Contact holes, or vias, on top of the poly-silicon 304 or gate electrode 308 are then formed in the interlayer dielectric 310 by photolithographic processes.

A second metal layer, known as the source electrode layer 312, is then deposited on the interlayer dielectric 310 and patterned. Where contact holes have been defined the source electrode contacts the gate electrode layer 306 or the poly-silicon layer 304.

A planarization layer 314 (e.g. acrylic resin) is then deposited on the second metal layer 312, which ensures that the surface of the device is flat. This is a key step for the ultrasound imager to create a well-defined and uniform cavity gap for the transducer.

Through holes, or vias, are then created in the planarization layer on top of the source electrode regions 312.

Then the deposition and patterning of the bottom electrode layer 316 is undertaken.

Figure 4B:
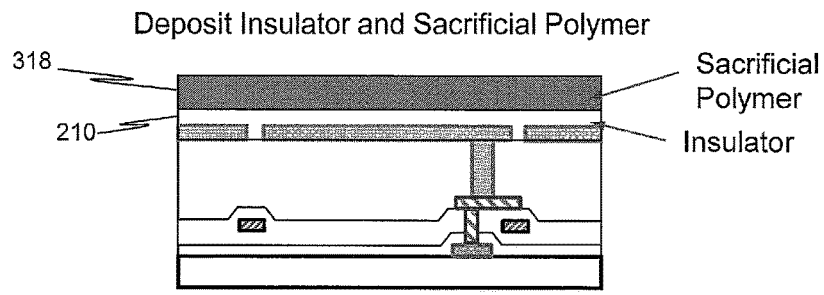
FIG. 4b shows the steps in fabricating an ultrasound transducer.
Figure 4C:
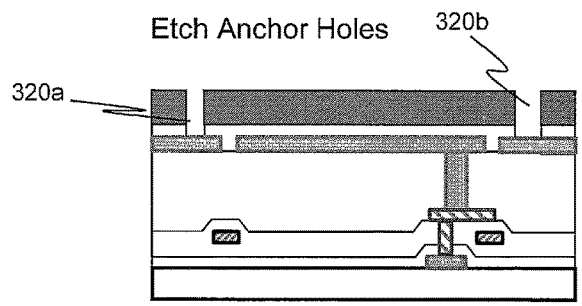
FIG. 4c shows the steps in fabricating an ultrasound transducer.
Figure 4D:
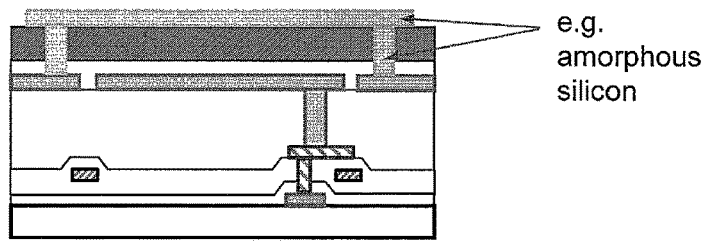
FIG. 4d shows the steps in fabricating an ultrasound transducer.
Figure 4E:
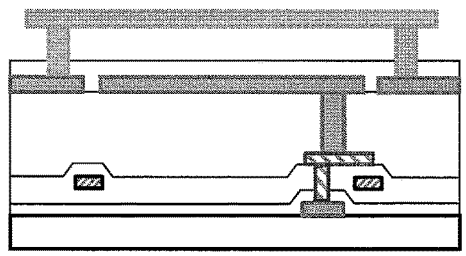
FIG. 4e shows the steps in fabricating an ultrasound transducer.
Figure 4F:
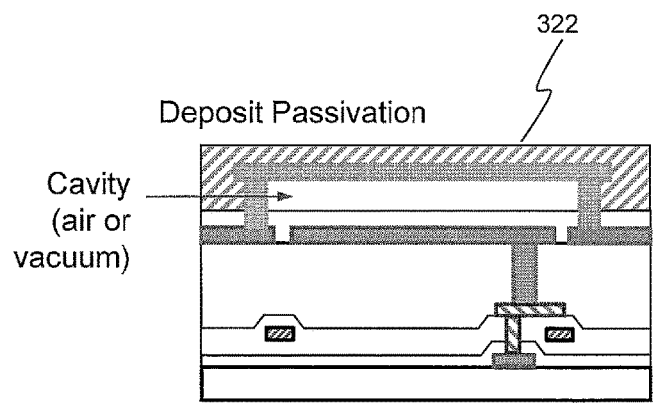
FIG. 4f shows the steps in fabricating an ultrasound transducer.

FIG. 4b-FIG. 4f show a more general schematic of the TFT portion, for simplicity. In FIG. 4b, an insulation layer 210 and a sacrificial polymer layer 318 are deposited on the TFT portion 202. In FIG. 4c, anchor holes 320a, 320b are etched into the sacrificial polymer layer 318 and the insulation layer 210. The anchor holes 320a, 320b expose the metal layer 218 of the TFT portion 202. In FIG. 4d, the supporting pillars 204a, 204b are deposited on the metal layer 218 to fill the anchor holes 302a, 302b. Further, the beam 206 is deposited onto the sacrificial polymer layer 318, such that it is in contact with the supporting pillars 204a, 204b. The beam 206 and the supporting pillars 204a, 204b may be manufactured from a silicon or poly silicon material. In exemplary transducers 102, the beam 206 and the supporting pillars 204a, 204b may be manufactured from amorphous silicon. In FIG. 4e, the sacrificial polymer layer is etched away. In FIG. 4f, a passivation layer 304 is deposited on the transducer 102. The passivation layer 322 may be deposited in a vacuum to leave a vacuum in the cavity 208.

The ultrasound transducer 102 described with reference to FIG. 3 and FIG. 4a-FIG. 4f may form part of the ultrasound sensor element 100 shown in FIG. 2a or FIG. 2b. Alternatively, the transducer 102 may be used in other ultrasound sensor elements.

Figure 5:
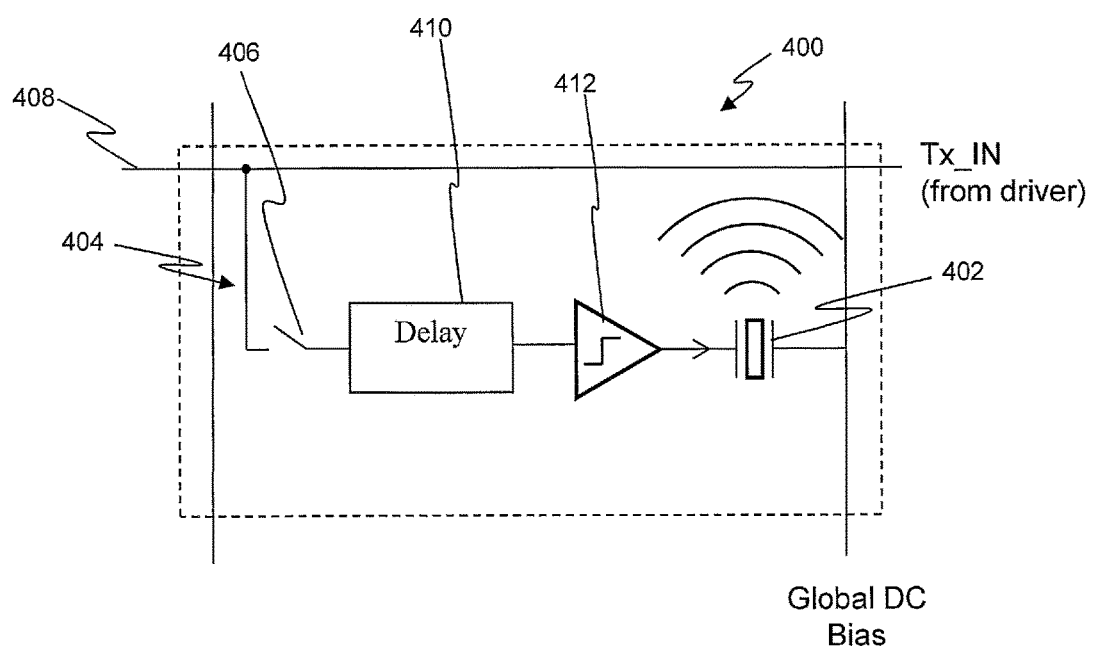
FIG. 5 is a schematic diagram of an ultrasound transmit sensor element.

FIG. 5 shows another ultrasound sensor element 400. The ultrasound sensor element 400 is a transmit sensor element. That is, the sensor element 400 comprises no receive circuit and is not capable of receiving reflected ultrasound signals. The transmit sensor element comprises a transducer 402 and a transmit circuit 404. The transducer may be the MEMs transducer discussed above in relation to FIG. 3 and FIG. 4a-FIG. 4f. The transmit circuit 402 is selectively enabled via a transmit enable switch 406, configured to connect the transmit circuit 402 to a transmit line 408 when closed. An input to a delay circuit 410 receives a transmit signal from the enable switch when it is in the closed position. The delay circuit 410 is configured to apply a delay to the transmit signal to provide ultrasound beam steering and/or beam focussing, as discussed below. The delay circuit 410 is configured to output a delayed transmit signal to a level shifter 412, which operates in a similar fashion to the level shifter 118 in the ultrasound sensor element 100 described above. In exemplary transmit ultrasound elements, the transmit circuit comprises one or more TFTs and specific transmit circuits are manufactured exclusively from TFTs.

In operation, a transmit signal is received from a driver and, if transmit sensor element is enabled by closing the switch 406, the transmit signal is received by the delay circuit 410. The delay circuit 410 delays the transmit signal by a specified amount of time in order to steer or focus the beam, as required. The delayed transmit signal is received by the level shifter 412, which produces a voltage sufficient to drive the transducer 402, which emits an ultrasound signal.

The removal of the receive circuit from the ultrasound sensor 400 provides sufficient room to include a delay circuit. This configuration means that the delay of each transmit pixel can be individually controlled.

The ultrasound sensor elements 100, 400 are configured to form part of an array of ultrasound sensor elements. The array of ultrasound sensors may have a number of rows in a range from 200 to 1500, in a range from 800 to 1200 or, in a specific array, 1000. The array of ultrasound sensors may have a number of rows in a range from 200 to 700, in a range from 400 to 600 or, in a specific array, 500.

Figure 6:
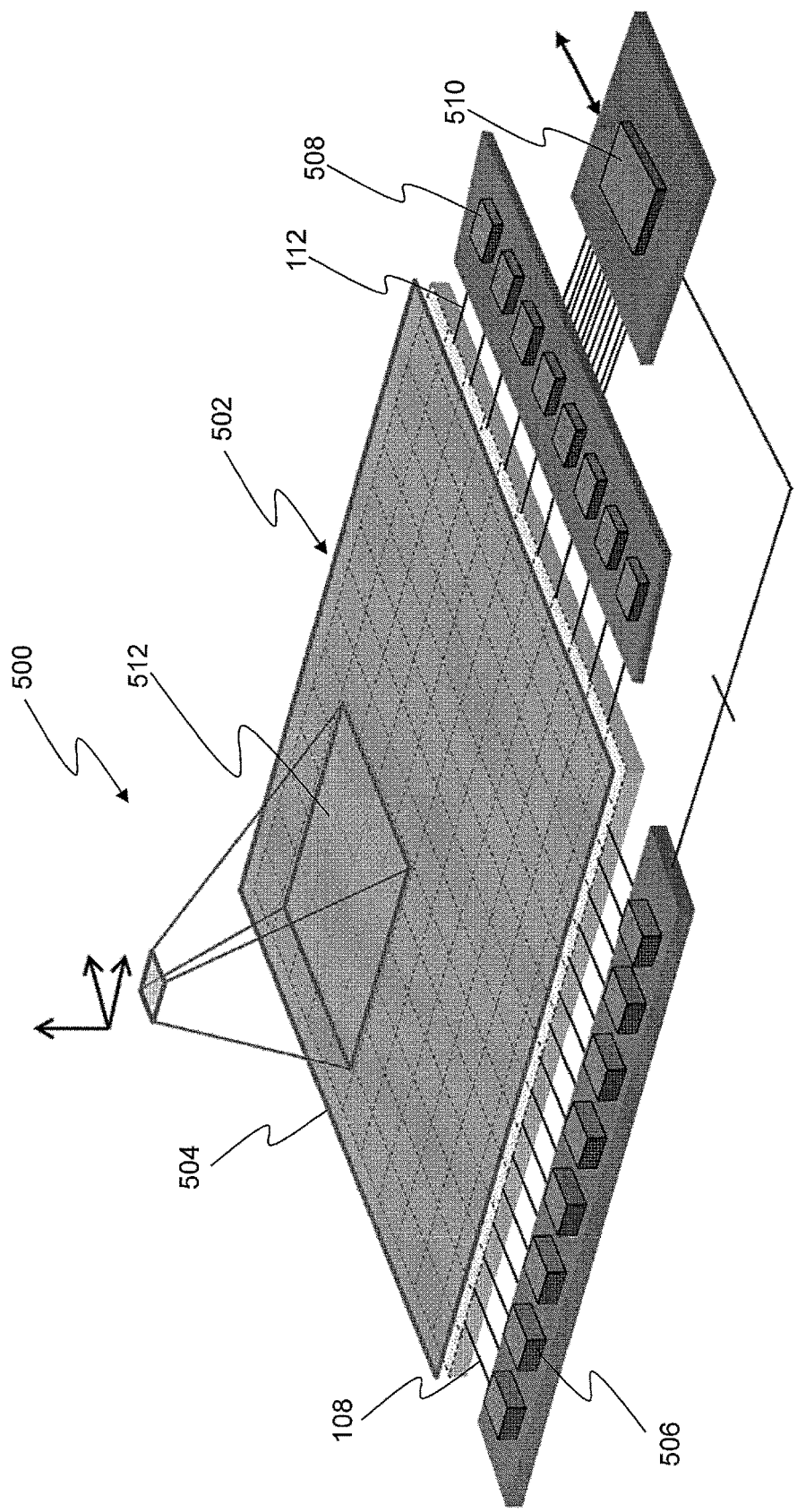
FIG. 6 is a schematic diagram of an ultrasound sensor element array assembly.

FIG. 6 shows an ultrasound sensor array assembly 500 comprising an array of ultrasound elements 502.

It is noted that the array of sensor elements 502 may be formed using one or more of any of the sensor elements disclosed herein. In the exemplary array assembly 500 of FIG. 6, the sensor elements are those referred to in FIG. 2a or FIG. 2b. However, the sensor elements 10 of FIG. 1a or FIG. 1b or sensor elements 400 of FIG. 5 or any other type of sensor element disclosed may be used.

The sensor array 502 comprises a plurality of sensor elements 100 arranged in columns and rows. A corresponding array of transducers 504 provides an emitting surface of the sensor array assembly 500. A non-emitting surface is the opposite surface to that on which the transducers 504 are positioned. As used herein, the terms "column" and "row" are for descriptive purposes only and do not imply any orientation.

A plurality of transmit driver circuits 506 are in electrical communication with the rows of the sensor array 502. Each transmit driver circuit 506 corresponds to a row of the array of sensor elements 504 and comprises a transmit delay circuit. The transmit driver circuits 506 are connected to each row of the sensor element array 502 by one of a plurality of transmit lines 108. The transmit driver circuits 506 provide the transmit signal on the transmit line 108 to instruct the enabled sensor elements in the corresponding row of the array 504 to transmit an ultrasound signal. The transmit driver circuits may include transmit delay circuits to delay the transmit signal for each row by a specified time for beam steering.

A plurality of receive driver circuits 508 are in electrical communication with the columns of the sensor array 502. Each receive driver circuit 508 corresponds to a column of the array of sensor elements 504 and comprises a receive delay circuit. The receive driver circuits 506 are connected to each column of the sensor element array 502 by one of a plurality of receive lines 112. The receive driver circuits 508 receive the current ($I_{COL}$) on the receive line 112 representing the summed received signal of each enabled sensor element in the corresponding column of the array 504. The receive driver circuits 508 include receive delay circuits to delay the received signal for each column by a specified time for beam steering. The receive driver circuits 508 send received signals to a system controller 510 for further processing.

The system controller 510 is in electrical communication with the transmit drivers 506 and the receive drivers 508 and is configured to control the transmission and receipt of ultrasound signals. The system controller 510 is configured to send instructions to the transmit drive circuits 506 to transmit an ultrasound pulse and to set the amount of delay on each row of the sensor element array 504. The system controller 510 is further configured to send instructions to receive driver circuits 508 to set the amount of delay to be applied to received signals from each column. The system controller 510 receives the signals from the receive driver circuits and sends them to other units of an imaging device for further processing, such as image rendering. The system controller 510 may also be configured to select which of the sensor elements 100 of the sensor element array 502 are enabled.

Therefore, the sensor element array assembly of FIG. 6 is able to provide a delayed transmit signal to each sensor element 100 in the array 502 and able to delay a received signal from each sensor element 100 in the array 502.

The assembly 500 comprises an array of sensor elements 502 and shows an exemplary architecture for a TFT based ultrasound imaging system. The assembly 500 comprises a transducer array 504 comprising elements to convert electrical input signals into acoustic output signals and to convert reflected acoustic signals back into electrical output signals. Close integration with control electronics is possible through the use of MEMs type transducers. The assembly 500 comprises a TFT active matrix 502 of transmit and receive circuits to generate control signals and sense the output of each transducer element in the array. The transmit and receive circuits are formed over a large area using thin-film transistor processes. Driver circuits 506, 508 at the edge of the active matrix 502 control the signal generation and receive processes. By creating the signal delays for beam-forming in the driver circuits 506, 508, the complexity of the transmit and receive circuits can be reduced. The system controller 510 provides signals to control the overall operation of the system, processes output data signals and communicates with the host device for recording and display of the generated images.

In order to successfully make a TFT based ultrasound imaging device the complexity of the transmit and receive circuits that are formed by the TFTs in each sensor element must be reduced.

It is noted that FIG. 6 is a schematic representation and may not accurately reflect the number of sensor elements, driver circuits and/or transmit and receive lines used in exemplary sensor array assemblies.

Because each of the sensor elements 100 may be selectively enabled, the transmit signals may be sent to a selected number of sensor elements 100 within each row. Similarly, the reflected signal may be received from a selected number of sensor elements within each column.

In operation, the system controller 510 sets the delay times to be applied to each of the transmit driver circuits 506 and receive driver circuits 508. The system controller 510 then instructs the transmit driver circuits 506 to transmit an ultrasound pulse. Each transmit driver circuit 506 sends a transmit signal, appropriately delayed, to all the sensor elements 100 on a row of the sensor element array 502. The sensor elements 100 that are enabled transmit an ultrasound pulse and receive reflected ultrasound signals. The received ultrasound signals are converted to an electrical current and, in each column in which receive circuits are enabled, all the received signals are summed and passed to the corresponding receive drive circuit 508. The receive drive circuit 508 applies the appropriate delay and passes the received signals to the system controller 510, which sends the received signals for further processing.

Figure 7:
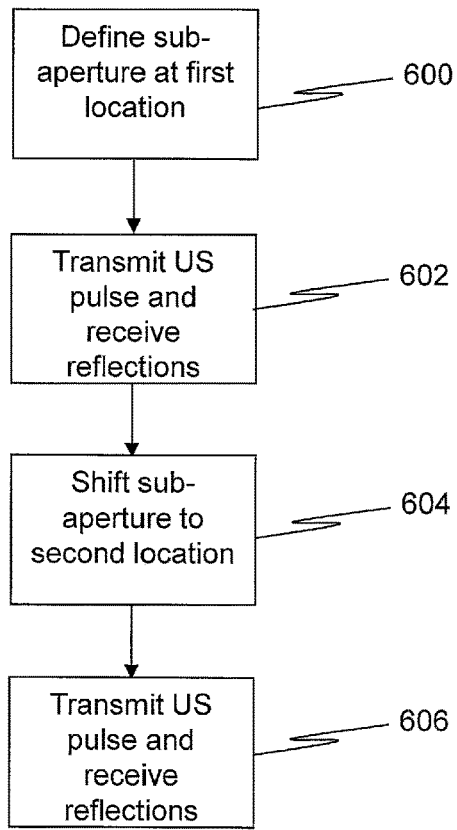
FIG. 7 is a flow diagram showing a method of performing an ultrasound scan.

FIG. 7 shows a method of performing an ultrasound scan. The method disclosed allows a 3D scan to be undertaken without the need to move the sensor element array.

Firstly, a sub-aperture 512 is defined 600 at a first location and the system controller enables the sensor elements 100 in the sub-aperture 512. The sub-aperture 512 comprises a plurality of adjacent sensor elements 100 fewer in number than the sensor elements 100 in the array 502. Exemplary sub-apertures may be a square of sensor elements 100. Exemplary sub-apertures may have a number of columns in a range from 50 to 200. Exemplary sub-apertures may have a number of rows in a range from 50 to 200. Specific exemplary sub-apertures may have 64 columns and 64 rows, or 128 columns and 128 rows. The sub-aperture will be positioned at a first location within the array 502 by virtue of the sensor elements 100 that have been enabled.

The enabled sensor elements 100 at the first location transmit an ultrasound pulse and receive reflected ultrasound signals 602. The system controller 510 instructs the transmit driver circuits 506 to transmit an ultrasound pulse and the driver circuits 506 send the transmit signal to the enabled sensor elements 100. The reflected signals received by the enabled sensor elements 100 at the first location are passed to the receive driver circuits 508 and then to the system controller 510.

The sub-aperture is shifted 604 to a second location within the array 502 by enabling another group of sensor elements 100. This is controlled by the system controller 510.

The enabled sensor elements 100 at the second location transmit an ultrasound pulse and receive reflected ultrasound signals 606. The system controller 510 instructs the transmit driver circuits 506 to transmit an ultrasound pulse and the driver circuits 506 send the transmit signal to the enabled sensor elements 100. The reflected signals received by the enabled sensor elements 100 at the second location are passed to the receive driver circuits 508 and then to the system controller 510.

In this way, a scan may be made across the entire area of the sensor element array 502 without the user having to move the array and, therefore, the emitted ultrasound beam.

In exemplary methods of performing an ultrasound scan, the delays applied to the enabled sensor elements 100 of the sub-aperture 512 by the transmit driver circuits 506 and the receive driver circuits 508 may be configured to shape the emitted and received ultrasound beams according to a 1D orthogonal scan pattern.

Figure 8A:
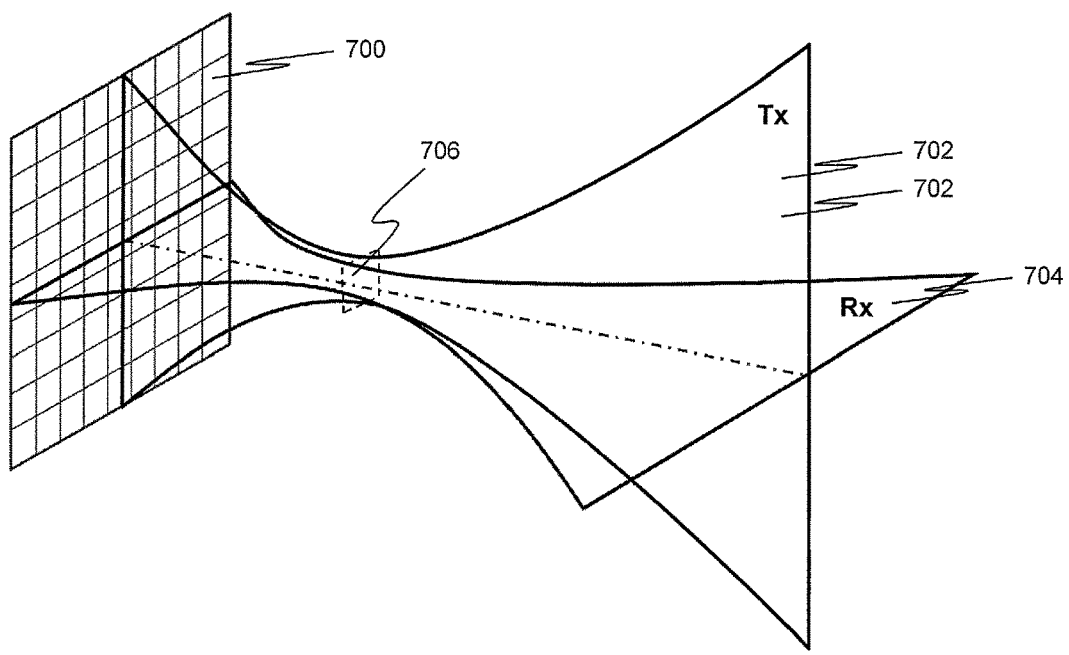
FIG. 8a is a schematic diagram showing a 1D orthogonal beam scan pattern.

FIG. 8a shows a 1D orthogonal scan pattern. The transmit signals to each row of the sensor element array 700 are delayed to produce a transmit beam 702 that forms a fan shape. This is a result of the fact that sensor elements 100 within each row of the sub-aperture 512 may not be delayed individually but must have identical delays. The reflected ultrasound signals are received at the array 700 and delays are applied to the received signal such that the receive beam 704 is effectively steered to provide fan, for the same reason as the transmit beam. The combined effect of this is to focus the ultrasound signal at a focal point 706 for the combined beams. When this method of scanning is used, the focal point 706 for the sub-aperture 512 may be the centre of the sub aperture 512, at some distance below it.

Figure 8B:
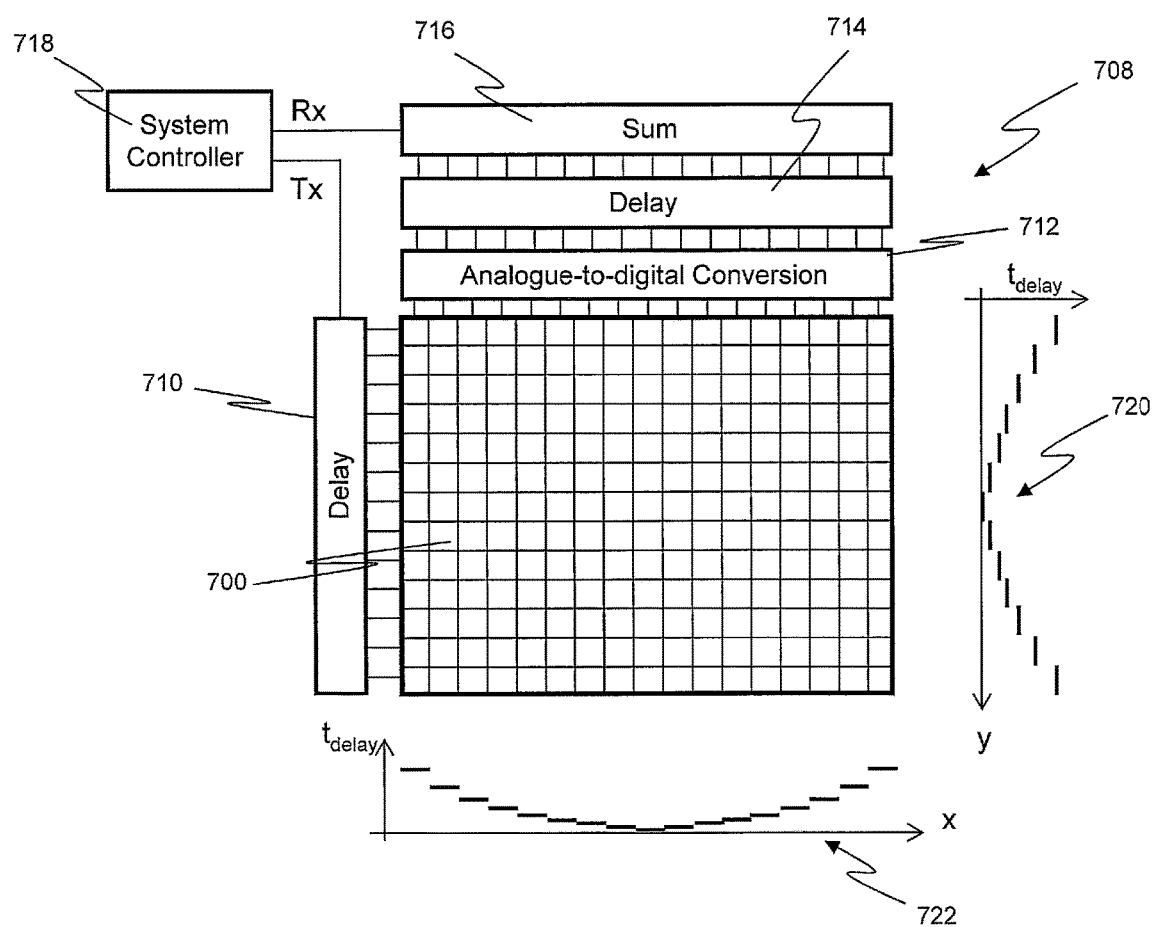
FIG. 8b is a schematic diagram of an ultrasound sensor element array assembly configured to produce a 1D orthogonal beam scan pattern.

FIG. 8b is a plan view of an ultrasound sensor element array assembly 708. The assembly 708 comprises a sensor element array 700, transmit delay circuitry 710, an analogue to digital converter (ADC) 712, receive delay circuitry 714, a summing unit 716 and a system controller 718. The transmit delay circuitry 710 is in electrical communication with each row of the array 700 and is configured to apply a delay to the transmit signal provided to each row. Each column of the array 700 is in electrical communication with the ADC 712 for sending receive signals to the ADC 712. The ADC 712 is configured to convert the analogue receive signals to a digital signal to be used by the system controller 718. The ADC 712 is in electrical communication with the receive delay circuitry 714, which is configured to apply a delay to the received signal provided by each column and pass the delayed signals to the summing unit 716. The summing unit 716 is configured to sum the delayed receive signals and pass them to the system controller 718. The system controller 718 is in electrical communication with the transmit delay circuitry 710 and the summing unit 716. The system controller is configured to program the transmit delay circuitry 710 and the receive delay circuitry 714 to apply the delay signals necessary to perform a 1D orthogonal scan pattern. The transmit delay signals for each of the rows of the array 700 are shown schematically in the plot 720. The receive delay signals for each of the columns of the array 700 are shown schematically in the plot 722.

When transmitting, the array 700 is configured so that each row of elements is driven in parallel using the same signal. This effectively makes the row into a single long element. The signals to each row pass via the programmable delay circuit 710 so that the signal may be focussed and steered. The result is a transmit signal which is focussed in elevation but not in azimuth 702. In receive, the array 700 connects so that columns are connected in parallel, with the received signals being amplified and sent down the columns to the receive ADCs 712 and delay circuits 714 at the edge of the array 700. Each column behaves as a single long element, resulting in a receive beam pattern which is focussed in azimuth but not in elevation 704.

Apodization is a term given to applying different amplitudes to different elements in the array 700. It can help to reduce side-lobe levels, at the expense of widening the main beam. Hanning apodization applies a raised-cosine profile to the amplitude of the array. The delay circuits 710, 714 may be programmable by the system controller 718 to implement apodization, such as Hanning apodization.

The operation of a plurality of sensor elements 100 in an array 502 using a 1D orthogonal beam-forming approach in pulse-echo mode and a MEMs type transducer is now described with reference to FIG. 2a-FIG. 2c and FIG. 6. It is noted that elements of the method described may be used with other sensor elements and/or sensor element arrays disclosed herein.

Low-voltage (e.g. 3V) transmit pulses are firstly applied to the transmit input signal lines 108 (TX_IN) for all active transmit rows by the driver circuits 509 at the edge of the active matrix 502. The transmit address lines 108 are arranged in a first direction, for example the row direction. Inactive transmit input signal lines 108 are held at a fixed potential, for example 0V.

Transmit enable control signals (TEN) are then used to connect the transmit circuits 104 of all elements 100 in a second direction to the transmit input signals via an enable switch transistor 110. For example, the transmit enable controls are arranged in the column direction with the transmit input signals in the row direction so that a sub-aperture of transmit pixels is formed. The transmit enable signal may also be used to connect the transmit circuit 104 to the transducer element 102 in each element 100 via the Tx/Rx switch 116.

The level shifter 118 that forms part of the transmit circuit 104 in the element amplifies the transmit input signal to a level suitable for driving the transducer 102, e.g. from 3V to 30V. After the transmit signal has been applied to all transducers 102 in the array (a time equal to the spatial-pulse length (SPL) plus the maximum delay) the transmit enable signals are made inactive.

The receive enable signals, REN, are made active to select the sub-aperture of receive elements. The receive enable signal connects the receive output amplifier 122 to the receive output signal line 112 (Rx_OUT). The receive enable signal may also be used to connect the transducer 102 to the receive circuit 106 in the sensor element 100. The receive enable signals are arranged in the first direction, orthogonal to the transmit enable signals and orthogonal to the receive output signal lines 112. For example, the receive enable signal lines and transmit input signal lines may be in the row direction whilst the receive output signal lines and transmit enable signal lines may be in the column direction.

Reflected ultrasound signals now cause the transducer 102 to generate an output signal. The magnitude of this signal may decay with time since the time taken for an echo to reach the transducer is proportional to depth and signals reflected from deeper features will be more heavily attenuated. A pre-amplifier 120 with time-gain compensation (TGC) may therefore optionally be used in each element 100. The TGC function allows the imaging system to have a much wider dynamic range than would otherwise be possible by preventing the signal from shallow features saturating and amplifying signals from deeper features.

The output amplifier 122, which may be a single transistor as shown in FIG. 2a, connects the pre-amplifier 120 to the receive output signal line 112, Rx_OUT. The output amplifier 122 converts the voltage input signal from the pre-amplifier 120 to a current output signal. The receive signals on one column are connected to the same output signal line and the currents of all active elements 100 on the column are therefore summed together.

Each receive output signal is converted into a digital signal by the analog-to-digital converter circuits in the driver circuits 508 at each column. Delays to each receive output signal are then digitally generated and all signals finally summed together.

Apodization may also be achieved in the system described above by controlling the power supply levels for the transmit circuits separately for each row.

In exemplary methods, the sub-aperture 512 may scan across an entire row of the array of sensor elements 502, with the sub-aperture 512 being shifted by any multiple of sensor elements 100 at a time, for example by one sensor element 100 each time. This produces a line of scan data across the row. The sub-aperture may be shifted down by one sensor element 100 and the adjacent row may then be scanned in the same way. In this way, scan data covering an area of the sensor array 502 may be provided.

Exemplary methods may further comprise re-steering the ultrasound beam to focus on a focal point 704 further away from or closer to the sensor element array 502. That is, a plurality of ultrasound pulses may be transmitted and reflected ultrasound signals received at each location of the sub-aperture, each time with the beam focussed to a different distance from the sensor element array 502. In this way, a scan of a 3D volume below the array 502 is able to be undertaken without the need to move the sensor array 502.

Use of the sub-aperture 512 reduces the amount of power that is wasted on each ultrasound pulse.

Figure 9A:
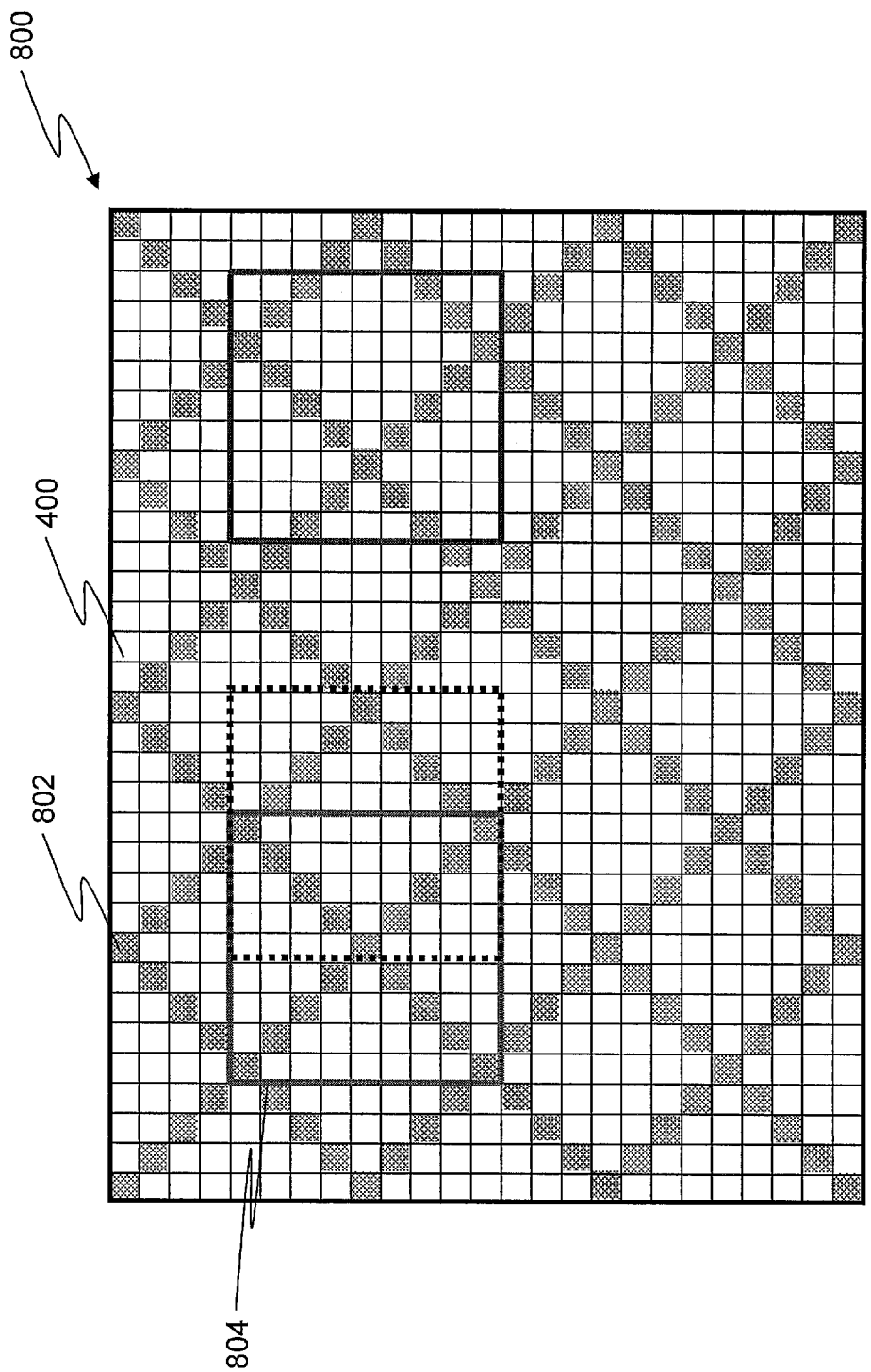
FIG. 9a is a schematic diagram of an ultrasound sensor element array.

FIG. 9a shows another array of ultrasound sensor elements 800.

The sensor elements of the array 800 comprise transmit sensor elements and receive sensor elements. In exemplary arrays 800, the transmit sensor elements 400 comprise the sensor elements of FIG. 5, described above. However, it is noted that any transmit sensor element having individual delay control may be used in the sensor array 800.

In FIG. 9a, the receive sensor elements 802 have been shaded and are arranged in orthogonal parallel diagonal lines across the array 800. That is, the receive sensor elements 802 have been arranged in a first series of parallel diagonal lines and a second series of parallel diagonal lines orthogonal to the first series. The receive sensor elements 802 form a "diamond" pattern on the array 800.

In the exemplary array 800 of FIG. 9a, the parallel diagonal lines of receive elements 802 are laterally spaced by N−1 sensor elements (in this example N=9 so the parallel diagonal lines of receive elements 802 are laterally spaced by eight sensor elements). As used here, the term "laterally" refers to the row and column directions of the array 800. The array of FIG. 9a is therefore suitable for use with an N×N square sub-aperture 804 (in this example a 9×9 square sub-aperture 804 since N=9). In this configuration where parallel diagonal lines of receive elements 802 are laterally spaced by N−1 sensor elements and the sub-aperture is an N×N sub-aperture, there will never be more than two receive sensor elements 802 in each row or column of the sub-aperture 804, no matter where the sub-aperture 804 is positioned in the array 800. That is, generally, the diagonal lines of receive elements 802 are laterally spaced by the number of sensor elements in the sub-aperture 804 minus one. The "cross" or "diamond" arrangement and the fact that there are never more than two receive sensor elements in one row or column of the sub-aperture means that the distance between a central axis (focal line) of the sub-aperture and the receive elements is the same. The same amount of delay may therefore be applied to both elements and so they may be connected to the same receive output signal line.

Alternatively, a pair of receive signal lines may be provided for each column and the two active elements may be connected to one of the pair of receive lines. Two receive driver circuits per column may be provided—for example located at either end of each column—and connected to one each of the pair of receive lines. A delay may therefore be provided uniquely for each receive element in the sub-aperture. This allows the ultrasound beam to be steered at an angle as well as translated. This is useful for some clinical applications e.g. cardiology where an image of the heart must be generated by steering the ultrasound beam through the intercostal spaces between ribs.

Figure 9B:
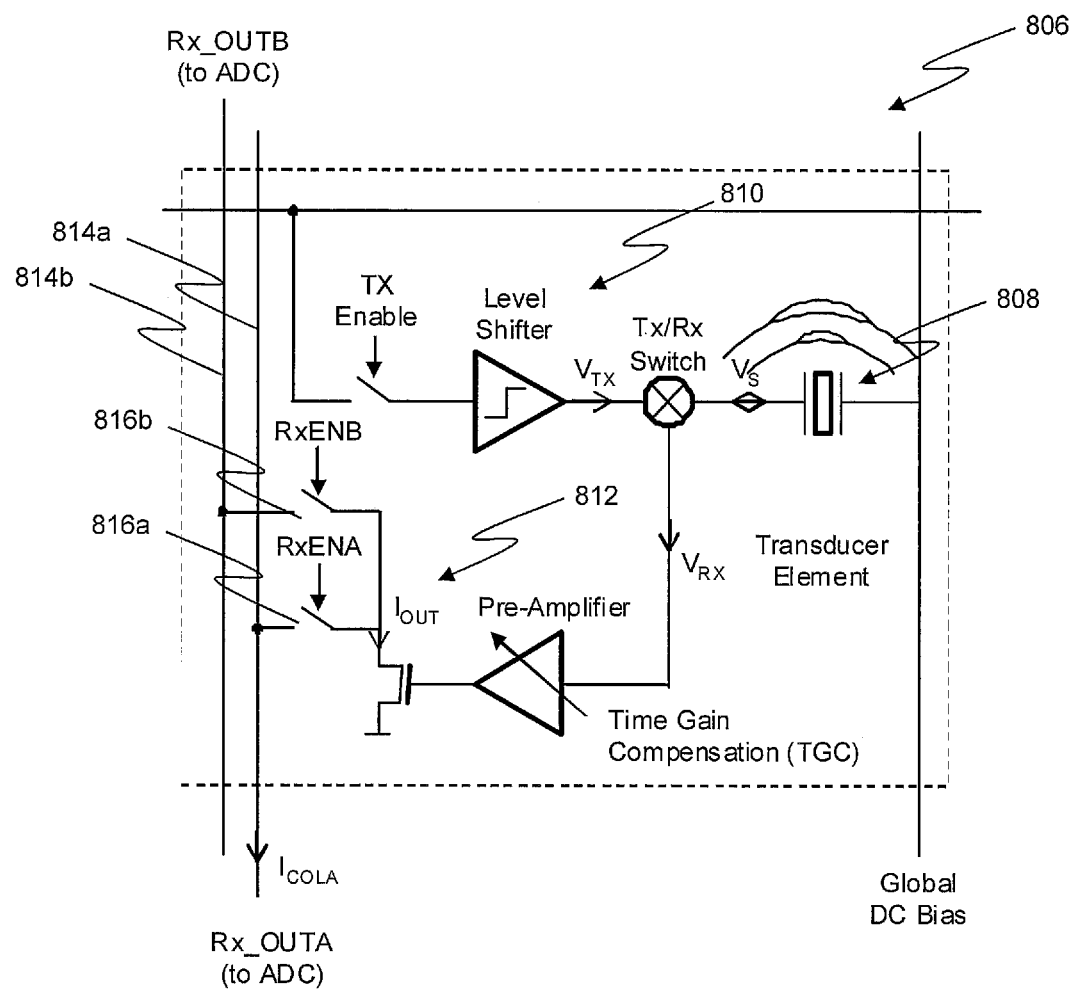
FIG. 9b is a schematic diagram of an ultrasound sensor element.

This arrangement is illustrated in FIG. 9b which shows an ultrasound sensor element 806 comprising an ultrasound transducer 808, a transmit circuit 810 configured to provide an electrical signal to the transducer for output of an ultrasound signal; and a receive circuit 812 configured to receive an electrical signal from the transducer, based on a received reflected ultrasound signal, wherein the transmit and receive circuits each comprise one or more thin film transistors, and wherein the receive circuit is selectively connectable to one of two receive lines 814a, 814b. The receive circuit 812 is selectively connectable to one of the two receive lines 814a, 814b by way of switches 816a, 816b.

In operation, the sub-aperture is scanned over the sensor element array 800 area to complete an ultrasound scan. The sub-aperture is defined and at a first location and, when the array 800 is included in an ultrasound sensor element assembly, a system controller enables the sensor elements 400, 802 of the sub-aperture. The system controller also determines and sets the required delay for each transmit sensor element 400 in the sub aperture in the first location such that the focal point of the ultrasound beam is below the centre of the sub-aperture. The transmit signal is sent to the transmit driver circuits and on to the transmit sensor elements 400 in the sensor array 800 and an ultrasound pulse is emitted. Reflected ultrasound signals are received at the receive sensor elements 804 of the array 802 and passed to the receive driver circuits and on to the system controller for further processing.

The receive driver circuits may include delay circuitry to impart a delay on the received signals for beam steering, as discussed above. The delays may be programmed into the delay circuitry by the system controller.

The sub-aperture is defined at a second location and the corresponding sensor elements 400, 802 are enabled. The system controller determines and sets a new required delay for each transmit sensor element 400 in the sub aperture at the second location such that the focal point of the ultrasound beam is below the centre of the sub-aperture. The transmit signal is sent to the transmit driver circuits and on to the transmit sensor elements 400 in the sensor array 800 and an ultrasound pulse is emitted. Reflected ultrasound signals are received at the receive sensor elements 802 of the array 800 and passed to the receive driver circuits and on to the system controller for further processing.

It is noted that elements of the method described with reference to FIG. 7 may be used when performing an ultrasound scan using the sensor array 800 of FIG. 9a. Focus is given to the features of the method that are different in the description above.

As the transmit sensor elements 400 may have their transmit signals delayed individually, the output ultrasound signal from each may be steered to any focal point. Therefore, no matter what the position of the sub-aperture, the transmit sensor elements 400 may be steered to a focal point, for example, in the centre of the sub-aperture at one of a plurality of depths. The received signals may also be steered by applying delays in the receive driver circuits at the edge of the matrix. The ability to steer on both transmit and receive in the aforementioned array minimizes the size of the focal point that can be achieved and allows high resolution images to be obtained.

In an alternative array, the transmit sensor elements have a cruciform arrangement and are arranged on the diagonals of the array. Since the number of delay elements is now small and there are, at most, two transmit elements per row, the delay for each transmit circuit may be provided at the edge of the array to enable the transmit beam to be focussed and steered. The remaining elements in the array are receive sensor elements and have no delay function implemented in the matrix. As a result the receive beam is a "plane wave" response pattern. Because the elements are hardwired to the transmit or receive circuits, shifting the sub-aperture will move the diagonal cross pattern into a number of asymmetric patterns. An advantage of this array is that therefore that the complexity and hence size of the circuits at each sensor element is reduced.

The arrays disclosed herein may be operated using a sub-aperture principle, with only a subset of the array being actively used. Moving the sub-aperture around the array allows the user to navigate to a region of interest. Using a synthetic aperture sequential beam-forming (SASB) approach, it also becomes possible to use sub-apertures to produce a slice image at a range of angles, rather than being constrained to the square grid of the array. By moving the sub-apertures both horizontally and vertically, it is possible to produce overlapping fixed-focus beams that can then be processed by SASB into a diagonal slice.

Figure 10:
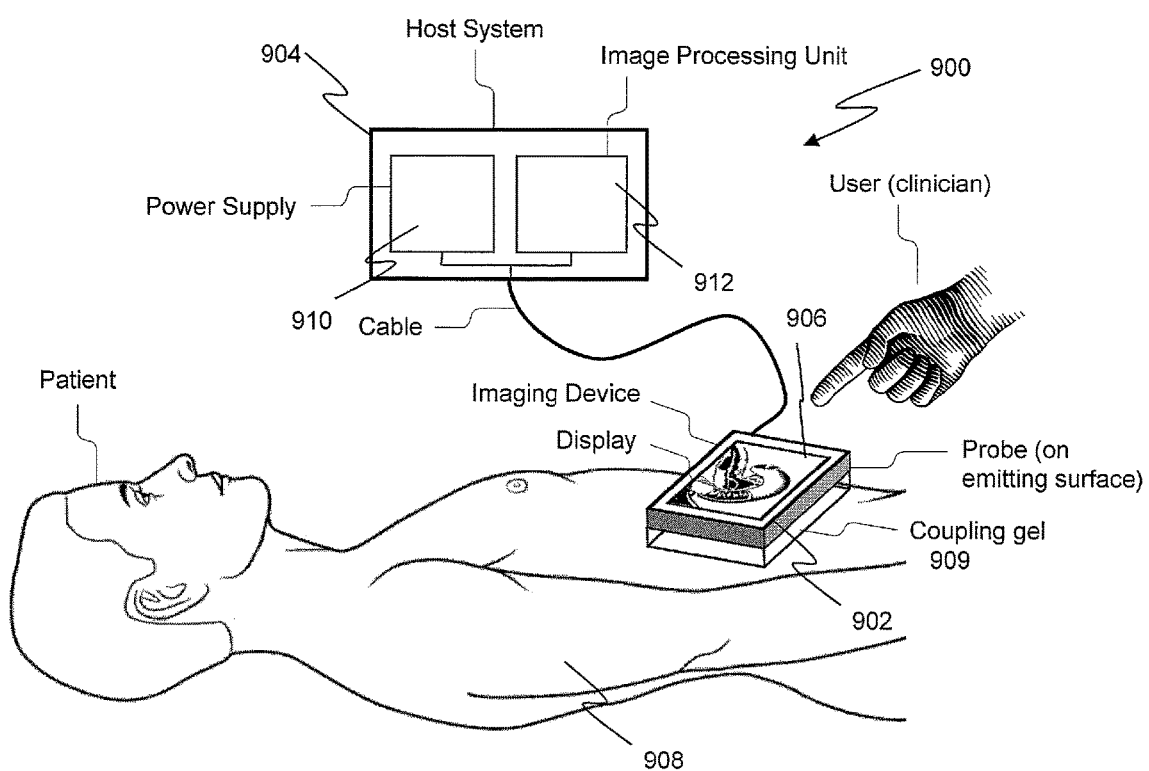
FIG. 10 is a representation of an ultrasound imaging device.

FIG. 10 shows an ultrasound imaging system 900. The imaging system 900 comprises an imaging device 902 and a host system 904. The imaging device 902 may comprise one or more of any of the sensor elements, transducers and sensor element array assemblies described above. Further, the imaging system 900 may use any of the methods of performing an ultrasound scan described above. The imaging device 902 comprises a display 906 positioned on a non-emitting surface of the imaging device 902. The imaging device 902 is shown positioned against a human subject 908 with the emitting surface of an array of ultrasound sensor elements facing the subject 908. Coupling gel 909 is positioned between the emitting surface of the imaging device 902 and the subject 908. The display 906 is located on the back of the imaging device 902, such that a user may get an image of what is within the human subject 908 directly beneath the area covered by the imaging device 902. This is analogous to holding a window against the subject 908, so that internal features can be viewed. The display 906 may comprise a liquid crystal display. The display 906 may comprise a touch screen.

The host system 904 comprises a power supply 910 and may optionally comprise an image processing unit 912. The image processing unit 912 may be configured to perform image processing from the received signals and may provide signalling to the display 906 to show the image. This removes the need for image processing capability to be included in the imaging device 902.

Figure 11:
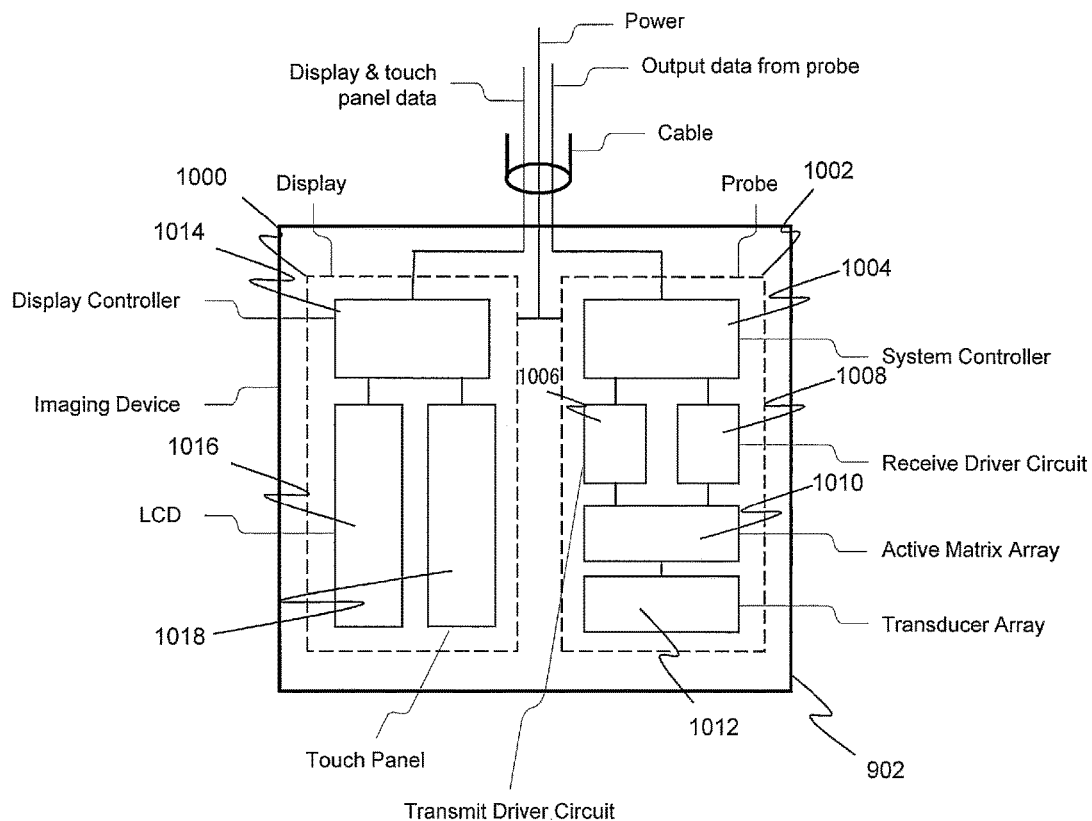
FIG. 11 is a schematic diagram of an ultrasound imaging device.

FIG. 11 is a block schematic diagram of an imaging device 902. The imaging device comprises a display circuit 1000 and a probe circuit 1002. The display circuit 1000 is configured to display images to a user. The probe circuit 1002 is configured to emit and receive ultrasound signals, as discussed above. In FIG. 11, the display circuit 1000 and the probe circuit 1002 are shown side-by-side for reasons of clarity, but this is not to be considered limiting on the configuration of imaging devices disclosed herein.

The probe circuit 1002 may receive power from the host system 904. The probe circuit comprises a system controller 1004, transmit driver circuitry 1006, receive driver circuitry 1008, an active matrix array 1010 and a transducer array 1012. The active matrix array 1010 and the transducer array 1012 may form a sensor element array as discussed above. The operation of the probe circuit 1002 may comprise any of the appropriate methods discussed above and is not described again here.

The display circuit comprises a display controller 1014, a display 1016 and, optionally, a touch panel 1018. The display controller 1014 is in electrical communication with the display 1016 and the touch panel 1018. The display controller 1014 is configured to provide signalling to the display 1016 to cause it to display an image. The display controller 1014 is further configured to receive user inputs from the touch panel 1018. The display controller 1014 is also in electrical communication with the image processing unit 912 in the host system 904 and is configured to receive display data therefrom and to transmit touch screen data thereto.

In operation, receive signals are passed by the system controller 1004 to the image processing unit 912 of the host system 904. The signals are processed into image data, which is passed to the display controller 1014, which generates display signals and transmits those to the display 1016 to instruct it to display an appropriate image. User input may be provided via the touch panel 1018 and passed to a processor of the host system via the display controller 1014.

Figure 12:
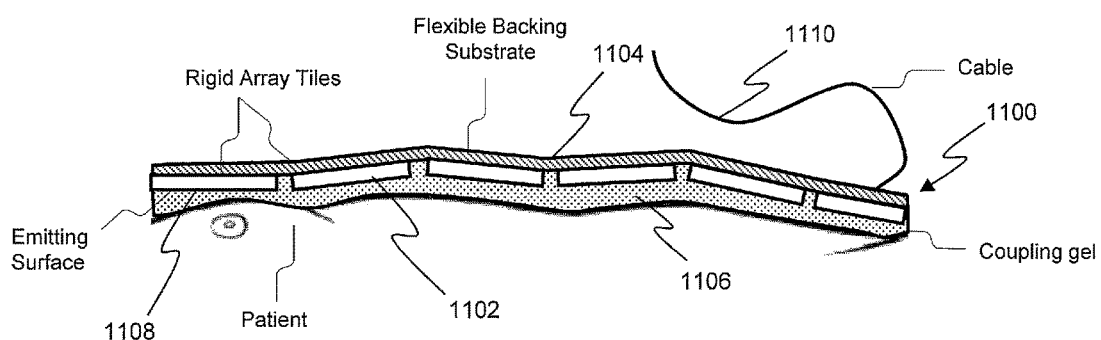
FIG. 12 is a schematic section through an ultrasound imaging device.
Figure 13:
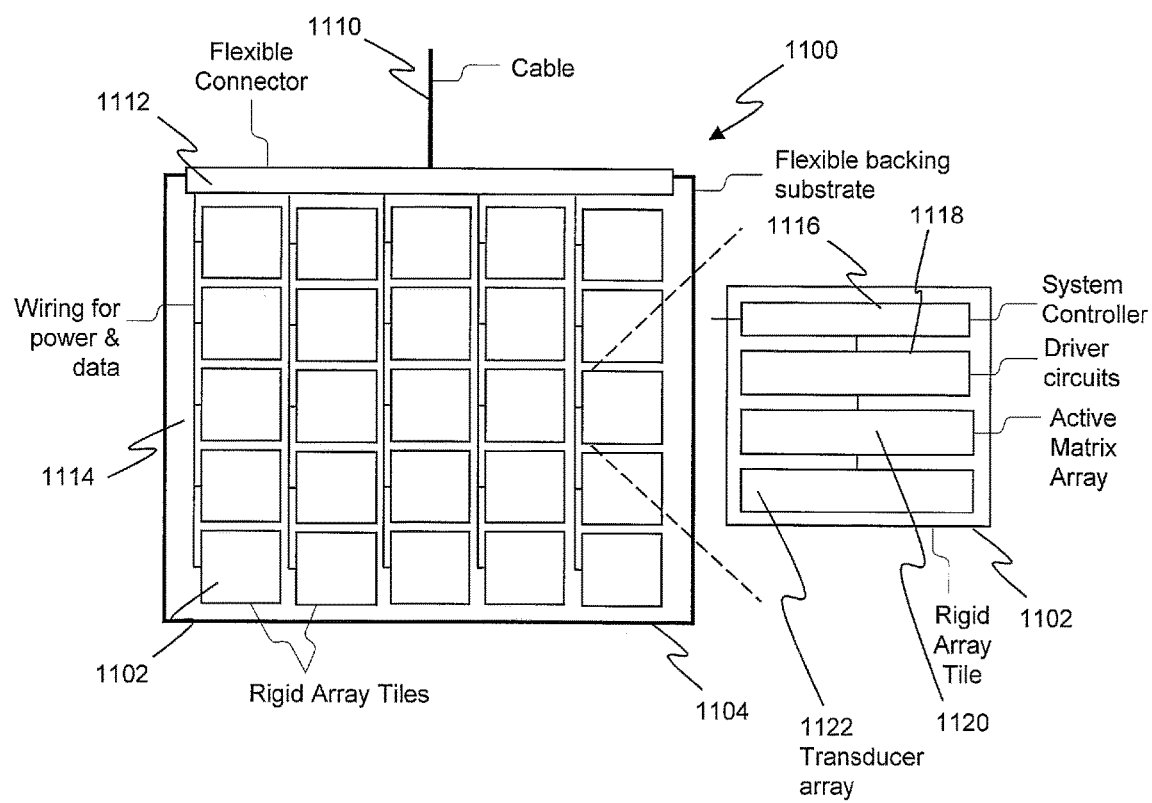
FIG. 13 is a schematic diagram of an ultrasound device.

FIG. 12 shows a schematic section through an imaging device 1100 and FIG. 13 shows a schematic plan view of the imaging device 1100. The imaging device 1100 may comprise one or more of any of the sensor elements, transducers and sensor element array assemblies described above. Further, the imaging device 1100 may use any of the methods of performing an ultrasound scan described above. The imaging device 1100 is conformable such that it may conform to the contours of a subject's body. In the exemplary imaging device 1100 of FIG. 12, rigid sensor element arrays 1102 are positioned on a flexible material 1104. Therefore, the imaging device 1100 is flexible and able to conform to the contours of the human subject. The sensor element arrays 1102 do not present a flat emitting surface emitting ultrasound into the subject, as the flexible material 1104 is curved and the arrays 1102 are therefore angled with respect to each other. Therefore, the beams from each of the sensor element arrays 1002 may be steered using delays to compensate. Coupling gel 1106 is located between an emitting surface 1108 of each sensor element array 1102 and the subject.

The imaging device 110 may be connected to a host system via a cable 1110 or via a wireless link. The cable 1110 may be connected to a flexible connector 1112 located on the flexible material 1104. Wiring 1114 for data and power to each of the sensor element arrays 1102 may be connected between the flexible connector 1112 and each array 1102 and incorporated into the flexible material.

FIG. 13 also shows an expanded schematic of a sensor element array 1102. The sensor element array 1102 comprises a system controller 1116, transmit/receive driver circuitry 1118, an active matrix array 1120 and a transducer array 1122. Operation of the sensor element array is as discussed above and is not repeated here.

In alternative imaging devices, the sensor element arrays may be fabricated on a flexible substrate.

A computer program may be configured to provide any of the above described methods. The computer program may be provided on a computer readable medium. The computer program may be a computer program product. The product may comprise a non-transitory computer usable storage medium. The computer program product may have computer-readable program code embodied in the medium configured to perform the method. The computer program product may be configured to cause at least one processor to perform some or all of the method.

Various methods and apparatus are described herein with reference to block diagrams or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

Computer program instructions may also be stored in a computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-ray (registered mark)).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and/or flowchart block or blocks.

Accordingly, the invention may be embodied in hardware and/or in software (including firmware, resident software, micro-code, etc.) that runs on a processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated.

According to an aspect of the invention, there is provided an ultrasound sensor element for use in a two dimensional array of ultrasound sensor elements. The sensor element comprises an ultrasound transducer. The sensor element further comprises a transmit circuit configured to provide an electrical signal to the transducer for output of an ultrasound signal. The sensor element further comprises a receive circuit configured to receive an electrical signal from the transducer, based on a received reflected ultrasound signal. The transmit and receive circuits each comprise one or more thin film transistors—and in the simplest case the transmit and receive circuits may each consist solely of one or more thin film transistors. The transmit circuit and the receive circuit are separate circuits from one another, and this allows transmission and reception to be controlled separately from one another, in contrast to prior art elements which have a single circuit for both transmission and reception.

Optionally, the transmit circuit and/or the receive circuit are configured to be selectively enabled. Since the transmit circuit and the receive circuit are separate circuits from one another, the transmit circuit and the receive circuit may be enabled independently from one another.

Optionally, the transmit circuit comprises a level shifter configured to receive an electrical signal at a first voltage and emit an electrical signal at a second voltage for operating the transducer to emit an ultrasound signal.

Optionally, the first voltage is in a range from 2 volts to 6 volts and the second voltage is in a range from 10 volts to 50 volts.

Optionally, the receive circuit comprises a pre-amplifier configured to receive and amplify an electrical signal from the transducer.

Optionally, the pre-amplifier is configured to control the amplification of the electrical signal received from the transducer using time-gain compensation.

Optionally, the receive circuit comprises an output amplifier configured to generate an output current.

Optionally, the receive circuit is selectively enabled by a receive enabling circuit configured to connect the receive circuit to one of a plurality of receive lines.

Optionally, the ultrasound transducer comprises a micro-electro-mechanical transducer.

Optionally, the micro-electro-mechanical transducer is a capacitive micromachined ultrasonic transducer.

According to an aspect of the invention, there is provided an ultrasound sensor array assembly comprising a two dimensional array of sensor elements described above. The array assembly further comprises a transmit delay circuit in electrical communication with each sensor element in a row of the array of sensor elements, wherein the transmit delay circuit is configured to delay a transmit signal to the sensor elements in the row.

Optionally, the sensor element array further comprises a plurality of transmit delay circuits, wherein each transmit delay circuit is in electrical communication with each sensor element in a row of the array of sensor elements, and wherein the transmit delay circuits are configured to delay a transmit signal to the sensor elements in each row for steering a beam of emitted ultrasound.

Optionally, the sensor element array further comprises a receive delay circuit in electrical communication with each sensor element in a column of the array of sensor elements, wherein the receive delay circuit is configured to delay a receive signal from the sensor elements in the row.

Optionally, the sensor element array further comprises a plurality of receive delay circuits, wherein each receive delay circuit is in electrical communication with each sensor element in a column of the array of sensor elements, and wherein the receive delay circuits are configured to delay a receive signal from the sensor elements in each row for steering the beam of received reflected ultrasound.

Optionally, the transmit delay circuits and the receive delay circuits are configured to undertake one dimensional orthogonal beam steering.

Optionally, the sensor element array is configured to emit an ultrasound signal from one or more sensor elements forming a sub-aperture of the array.

According to an aspect of the invention, there is provided an ultrasound transmit sensor element for inclusion in a two dimensional array of ultrasound sensor elements. The sensor element comprises an ultrasound transducer. The sensor element further comprises a transmit circuit comprising one or more thin film transistors and configured to provide an electrical signal to the transducer for output of an ultrasound signal. The sensor element further comprises a delay circuit configured to delay a transmit signal for the ultrasound transducer.

Optionally, the delay circuit comprises one or more thin film transistors.

According to an aspect of the invention, there is provided a sensor array assembly comprising an array of sensor elements, as described above, wherein the delay circuits of the transmit elements are configurable to provide beam steering.

Optionally, the array further comprises a plurality of receive sensor elements configured to receive reflected ultrasound signals.

Optionally, the transmit sensor elements and the receive sensor elements are arranged such that a sub-aperture of fixed dimensions includes no more than two receive sensor elements in each column of sensor elements.

Optionally, the receive elements are arranged in a plurality of orthogonal parallel diagonal lines across the array.

Optionally, the sub-aperture is a N×N square, and wherein each diagonal line of receive sensor elements is laterally offset from an adjacent diagonal line of receive sensor elements by N−1.

According to an aspect of the invention, there is provided an ultrasound imaging device comprising an array of sensor elements, as described above.

Optionally, the device further comprises a display positioned on a non-emitting side of the array. Optionally, the display comprises a liquid crystal display.

Optionally, the array is conformable, such that it may conform at least partially to the contours of a surface against which it is placed.

Optionally, the sensor elements of the array are formed on a flexible substrate.

Optionally, the sensor elements are positioned on a flexible material.

According to an aspect of the invention, there is provided an ultrasound imaging device. The ultrasound imaging device comprises a two dimensional array of ultrasound sensor elements configured to emit ultrasound signals and receive reflected ultrasound signals and a display positioned on a non-emitting side of the array.

According to an aspect of the invention, there is provided an ultrasound imaging device comprising a two dimensional array of ultrasound sensor elements configured to emit ultrasound signals and receive reflected ultrasound signals, wherein the array is conformable, such that it may conform at least partially to the contours of a surface against which it is placed.

According to an aspect of the invention, there is provided an ultrasound transducer. The transducer comprises a micro-electro-mechanical system portion vibratable for emitting an ultrasound signal and a thin film transistor portion configured to drive electro-statically the micro-electro-mechanical system portion to cause it to vibrate.

According to an aspect of the invention, there is provided a method of performing an ultrasound scan using a two dimensional array of sensor elements. The method comprises defining a sub-aperture of sensor elements in a first location within the array of sensor elements. The method further comprises transmitting an ultrasound signal and receiving reflected ultrasound signals using the sensor elements of the sub-aperture at the first location. The method further comprises shifting the sub-aperture to a second location within the array of sensor elements. The method further comprises transmitting an ultrasound signal and receiving reflected ultrasound signals using the sensor elements of the sub-aperture at the second location.

Optionally, the method further comprises a plurality of sub-aperture shifts to perform a scan using all the sensor elements in the array of sensor elements.

Optionally, the sub-aperture is shifted by one sensor element at each sub-aperture shift.

Optionally, the sub-aperture is shifted from one side of a row of the array of sensor elements to the other to perform a scan of the row.

Optionally, after the row has been scanned, the sub-aperture is shifted to an adjacent row to perform a scan of the adjacent row.

Optionally, the two dimensional array of sensor elements comprises one or more sensor elements having an ultrasound transducer, a transmit circuit configured to provide an electrical signal to the transducer for output of an ultrasound signal and a receive circuit configured to receive an electrical signal from the transducer, based on a received reflected ultrasound signal, wherein the transmit and receive circuits each comprise one or more thin film transistors.

Optionally, the two dimensional array of sensor elements comprises a plurality of transmit sensor elements and a plurality of receive sensor elements, wherein the transmit sensor elements comprise a transmit circuit and a delay circuit configured to delay a transmit signal for an ultrasound transducer.

Optionally, the transmit circuit and/or the delay circuit comprise one or more thin film transistors.

Optionally, the two dimensional array of sensor elements is arranged such that the sub-aperture comprises no more than two receive sensor elements in each column and row, each receive sensor element being selectively connectable to two receive lines. The method may further comprise connecting the receive sensor elements in a column of the sub-aperture to different receive lines.

According to an aspect of the invention, there is provided a non-transitory computer readable medium comprising computer readable code configured to carry out any of the methods defined above.

The methods and apparatus disclosed herein aim to mitigate or overcome some of the disadvantages of existing ultrasound imaging technologies.

The inventors have appreciated that a TFT-based ultrasound sensor element has the potential to enable expansion of ultrasound imaging from secondary care to mass volume primary care and the developing world. Further, TFT-based ultrasound sensor elements allow for larger arrays of sensor elements.

The concept of ultrasound imaging using apparatus comprising thin film transistors to form transmit and receive circuits of an ultrasound probe has certain advantages that will be discussed in detail herein. Further aspects of the invention including the ultrasound signal beam-forming methods, pixel circuit designs and integration with MEMs type transducers provide additional benefits.

According to an aspect the invention, there is provided an ultrasound imaging device including an array of transmit and receive circuits comprising thin-film transistors.

Each feature disclosed or illustrated in the present specification may be incorporated in the invention, whether alone or in any appropriate combination with any other feature disclosed or illustrated herein.

The skilled person will be able to envisage other embodiments without departing from the scope of the appended claims.

INDUSTRIAL APPLICABILITY

The ultrasound imaging methods and apparatus of the present invention may be used in many applications including, for example, medical imaging.

The invention claimed is:

1. An ultrasound sensor array assembly comprising a two dimensional array of ultrasound sensor elements, each sensor element in the two dimensional array of ultrasound sensor elements comprising:
   an ultrasound transducer,
   a transmit circuit configured to provide an electrical signal to the transducer for output of an ultrasound signal; and
   a receive circuit configured to receive an electrical signal from the transducer, based on a received reflected ultrasound signal,
   wherein the transmit and receive circuits each comprise one or more thin film transistors;
   the sensor array assembly further comprising:
   a plurality of transmit delay circuits, wherein each transmit delay circuit is in electrical communication with each sensor element in a row of the array of sensor elements, and wherein the transmit delay circuits are configured to delay a transmit signal to the sensor elements in each row for steering a beam of emitted ultrasound; and
   a plurality of receive delay circuits, wherein each receive delay circuit is in electrical communication with each sensor element in a column of the array of sensor elements, and wherein the receive delay circuits are configured to delay a receive signal from the sensor elements in each column for steering the beam of received reflected ultrasound;
   wherein the plurality of transmit delay circuits are incorporated into a first driver circuit, and the plurality of receive delay circuits are incorporated into a second driver circuit, and the first and second driver circuits are located external and adjacent to the two dimensional array of ultrasound sensor elements.

2. The sensor array assembly according to claim 1, wherein at least one of the transmit circuit or the receive circuit is configured to be selectively enabled.

3. The sensor array assembly according to claim 1, wherein the transmit circuit comprises a level shifter configured to receive an electrical signal at a first voltage and emit an electrical signal at a second voltage for operating the transducer to emit an ultrasound signal.

4. The sensor array assembly according to claim 1, wherein the receive circuit comprises a pre-amplifier configured to receive and amplify an electrical signal from the transducer.

5. The sensor array assembly according to claim 1, wherein the receive circuit comprises an output amplifier configured to generate an output current.

6. The sensor array assembly according to claim 2, wherein the receive circuit is selectively enabled by a receive enabling circuit configured to connect the receive circuit to one of a plurality of receive lines.

7. The sensor array assembly according to claim 1, wherein the ultrasound transducer comprises a micro-electro-mechanical transducer.

8. The sensor array assembly according to claim 1, wherein the transmit delay circuits and the receive delay circuits are configured to undertake one dimensional orthogonal beam steering.

9. The sensor array assembly according to claim 1, configured to emit an ultrasound signal from one or more sensor elements forming a sub-aperture of the array.

10. An ultrasound imaging device comprising an ultrasound sensor array according to claim 1.

11. The ultrasound imaging device according to claim 10, wherein the two dimensional array of ultrasound sensor elements configured to emit ultrasound signals and receive reflected ultrasound signals is conformable, such that it may conform at least partially to the contours of a surface against which it is placed.

12. The sensor array assembly according to claim 1, further comprising a switch that switches between connecting the transducer to the transmit circuit or to the receive circuit;
   wherein the switch comprises a first switch transistor that is connected to the transmit circuit for actuating the transmit circuit based on a transmit switch control signal, and a second switch transistor that is connected to the receive circuit for actuating the receive circuit based on a receive switch control signal; and
   wherein terminals of the first switch transistor and the second switch transistor are electrically connected to the transducer at a common node.

* * * * *